United States Patent
Barry, III et al.

(10) Patent No.: US 7,547,519 B2
(45) Date of Patent: Jun. 16, 2009

(54) METHODS OF DIAGNOSING MULTIDRUG RESISTANT TUBERCULOSIS

(75) Inventors: Clifton E. Barry, III, Bethesda, MD (US); Andrea E. DeBarber, Rockville, MD (US); Khisimuzi Mdluli, Seattle, WA (US); Linda-Gail Bekker, New York, NY (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 309 days.

(21) Appl. No.: 11/058,484

(22) Filed: Feb. 14, 2005

(65) Prior Publication Data

US 2005/0142602 A1 Jun. 30, 2005

Related U.S. Application Data

(62) Division of application No. 09/888,320, filed on Jun. 22, 2001, now Pat. No. 6,905,822.

(60) Provisional application No. 60/214,187, filed on Jun. 26, 2000.

(51) Int. Cl.
 *G01N 33/53* (2006.01)
 *G01N 33/00* (2006.01)
(52) U.S. Cl. ............... 435/7.1; 435/7.2; 435/7.6; 435/7.92
(58) Field of Classification Search ............ 435/7.1
 See application file for complete search history.

(56) References Cited

U.S. PATENT DOCUMENTS 6,294,328 B1 * 9/2001 Fleischmann et al. ........ 435/6

OTHER PUBLICATIONS

Cole et al, *Mycobacterium tuberculosis* H37Rv complete genome Accession # BX842584/c, 1998, GenEmbl, 6 pages.*

Cole et al, *Mycobacterium tuberculosis* H37Rv complete genome Accession # C70655, 1998, GenEmbl, 3 pages.*

Banerjee et al, inhA, a gene encoding a target for isoniazid and ethionamide in *Mycobacterium tuberculosis*. 1994, Science, vol. 263, p. 227-30.*

Ahern, et al., "Biochemical, Reagent Offer Scientests Good Return on Investment," *The Scientist*, 1995, p. 20, vol. 9, No. 15.

Badcock, et al., Sanger Centre Wellcome Genome Campus, Direct Submission, Accession No. 283864, Jan. 14, 1997, 23 pages.

Boehringer Mannheim 1997 Biochemicals Catalog, p. 95.

DeBarber et al., "Ethionamide activation and sensitivity in multidrug-resistant *Mycobacterium tuberculosis*," *PNAS*, Aug. 2000, pp. 9677-9682, vol. 97, No. 17.

Morlock, G., et al., "ethA, inhA, and katG Loci of Ethionamide-Resistant Clinical *Mycobacterium tuberculosis* Isolates," *Antimicrobial Agents and Chemotherapy*, Dec. 2003, pp. 3799-3805.

Phillip, et al., "An integrated map of the genome of the tubercle bacillus, *Mycobacterium tuberculosis* H37Rv, and comparison with Mycobacterium leprae," *PNAS*, Apr. 1996, pp. 3121-3137, vol. 93.

Sreevatsan, S., et al., "Restricted structural gene polymorphism in the *Mycobacterium tuberculosis* complex indicates evolutionarily recent global dissemination," *Proc. Natl. Acad. Sci.* USA, Sep. 1997, pp. 9869-9874, vol. 94.

* cited by examiner

*Primary Examiner*—Mark Navarro
(74) *Attorney, Agent, or Firm*—Townsend and Townsend and Crew LLP

(57) ABSTRACT

The invention relates to the discovery that a putative gene of *Mycobacterium tuberculosis* with no previously identified function is responsible for the ability of the bacterium to activate thioamide drugs. Since *M. tuberculosis* has a low rate of synonymous mutations, all mutations in this gene, identified as Rv3854c and now termed "EtaA," are expected to inhibit the ability of a bacterium with the mutation to activate a thioamide or thiocarbonyl drug. Thus, detecting a bacterium with a mutation in this gene indicates that the bacterium is resistant to treatment with thioamides.

13 Claims, 6 Drawing Sheets

| Strain | ETA | TA | TC | INH | Nucleotide | Amino-acid |
|---|---|---|---|---|---|---|
| AS1TAg | H | H | H | S | 65 | - |
| AS2TAg | H | H/M | M | H | 127 | G43→C |
| AS3TAg | L | H | H | H | 152 | P51→K |
| AS4TAg | L | L/M | L | M | 173 | D58→A |
| AS5TAg | L | H | H | M | 250 | Y84→D |
| AS6TAg | L | M | L | M | 811 | - |
| AS7TAg | L | L | S | H | 1025 | T342→K |
| AS8TAg | L | L | M | M | 1025 | T342→K |
| AS9TAg | L | L | M | M | 1025 | T342→K |
| AS10TAg | M | H | H | H | 1141 | A381→P |
| AS11TAg | H | H | H | S | 1141 | A381→P |
| AS12TAg | S | H | H | M | - | - |
| AS13TAg | S | H | M | S | - | - |
| AS14TAg | S | S | H | M | - | - |
| ATCC3580 | H | - | - | - | 557 | T186→K |

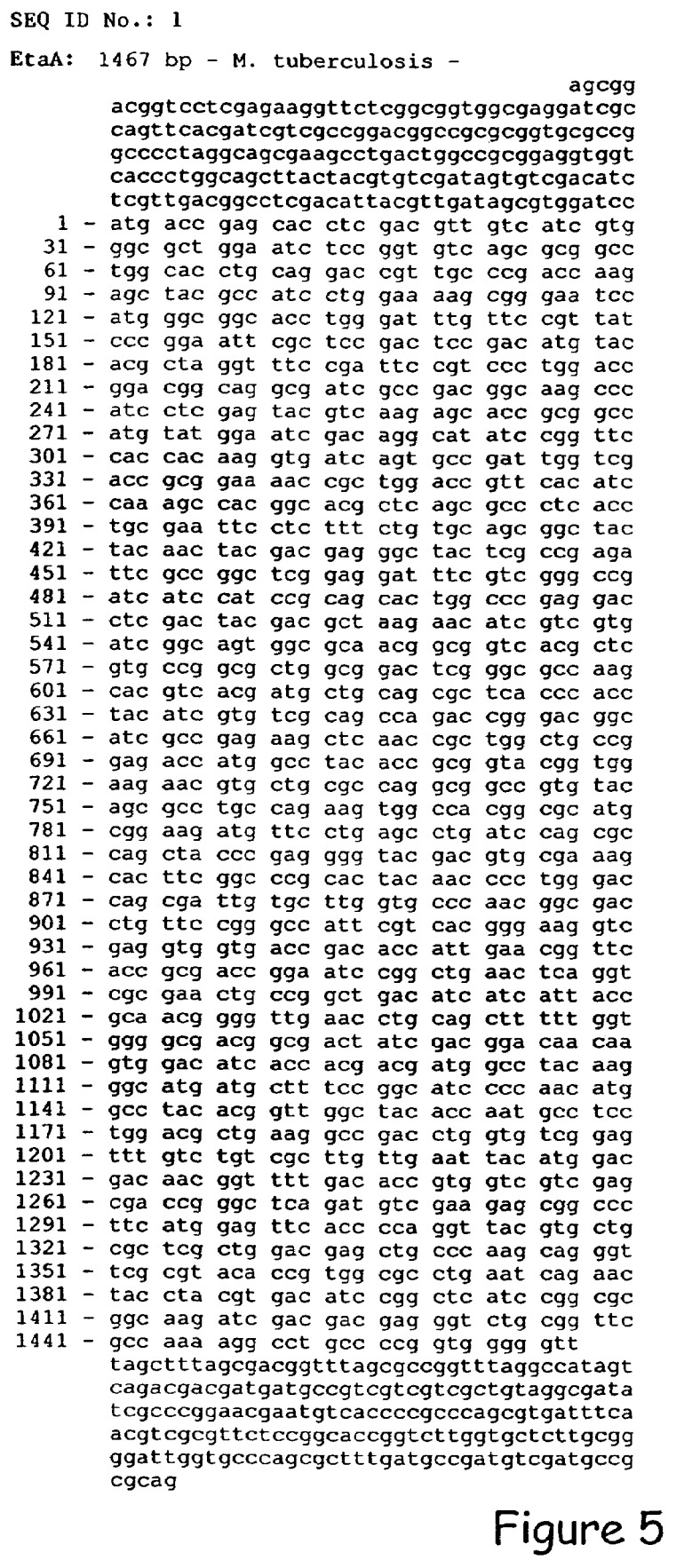

SEQ ID No.: 1

EtaA: 1467 bp - M. tuberculosis -

```
                                                   agcgg
        acggtc

SEQ ID No.: 2

EtaA: 489 aa - M. tuberculosis -

```
  1 - MTEHLDVVIV GAGISGVSAA WHLQDRCPTK SYAILEKRES MGGTWDLFRY PGIRSDSDMY
 61 - TLGFRFRPWT GRQAIADGKP ILEYVKSTAA MYGIDRHIRF HHKVISADWS TAENRWTVHI
121 - QSHGTLSALT CEFLFLCSGY YNYDEGYSPR FAGSEDFVGP IIHPQHWPED LDYD

SEQUENCE LISTING

```
<160> NUMBER OF SEQ ID NOS: 16

<210> SEQ ID NO 1
<211> LENGTH: 1867
<212> TYPE: DNA
<213> ORGANISM: Mycobacterium tuberculosis
<220> FEATURE:
<221> NAME/KEY: CDS
<222> LOCATION: (201)..(1670)
<223> OTHER INFORMATION: wild-type EtaA monooxygenase (Rv3854c, EthA)
<223> OTHER INFORMATION: EtaA

<400> SEQUENCE: 1
agcggacggt cctcgagaag gttctcggcg gtggcgagga tcgccagttc acgatcgtcg     60
```

```
                                       -continued ccggacggcc gcgcggtgcg ccggcccta ggcagcgaag cctgactggc cgcggaggtg      120
gtcaccctgg cagcttacta cgtgtcgata gtgtcgacat ctcgttgacg gcctcgacat    180
tacgttgata gcgtggatcc atg acc gag cac ctc gac gtt gtc atc gtg ggc    233
                        Met Thr Glu His Leu Asp Val Val Ile Val Gly
                          1               5                      10 gct gga atc tcc ggt gtc agc gcg gcc tgg cac ctg cag gac cgt tgc      281
Ala Gly Ile Ser Gly Val Ser Ala Ala Trp His Leu Gln Asp Arg Cys
             15                  20                  25 ccg acc aag agc tac gcc atc ctg gaa aag cgg gaa tcc atg ggc ggc      329
Pro Thr Lys Ser Tyr Ala Ile Leu Glu Lys Arg Glu Ser Met Gly Gly
         30                  35                  40 acc tgg gat ttg ttc cgt tat ccc gga att cgc tcc gac tcc gac atg      377
Thr Trp Asp Leu Phe Arg Tyr Pro Gly Ile Arg Ser Asp Ser Asp Met
     45                  50                  55 tac acg cta ggt ttc cga ttc cgt ccc tgg acc gga cgg cag gcg atc      425
Tyr Thr Leu Gly Phe Arg Phe Arg Pro Trp Thr Gly Arg Gln Ala Ile
 60                  65                  70                  75 gcc gac ggc aag ccc atc ctc gag tac gtc aag agc acc gcg gcc atg      473
Ala Asp Gly Lys Pro Ile Leu Glu Tyr Val Lys Ser Thr Ala Ala Met
                 80                  85                  90 tat gga atc gac agg cat atc cgg ttc cac cac aag gtg atc agt gcc      521
Tyr Gly Ile Asp Arg His Ile Arg Phe His His Lys Val Ile Ser Ala
             95                 100                 105 gat tgg tcg acc gcg gaa aac cgc tgg acc gtt cac atc caa agc cac      569
Asp Trp Ser Thr Ala Glu Asn Arg Trp Thr Val His Ile Gln Ser His
         110                 115                 120 ggc acg ctc agc gcc ctc acc tgc gaa ttc ctc ttt ctg tgc agc ggc      617
Gly Thr Leu Ser Ala Leu Thr Cys Glu Phe Leu Phe Leu Cys Ser Gly
     125                 130                 135 tac tac aac tac gac gag ggc tac tcg ccg aga ttc gcc ggc tcg gag      665
Tyr Tyr Asn Tyr Asp Glu Gly Tyr Ser Pro Arg Phe Ala Gly Ser Glu
140                 145                 150                 155 gat ttc gtc ggg ccg atc atc cat ccg cag cac tgg ccc gag gac ctc      713
Asp Phe Val Gly Pro Ile Ile His Pro Gln His Trp Pro Glu Asp Leu
                 160                 165                 170 gac tac gac gct aag aac atc gtc gtg atc ggc agt ggc gca acg gcg      761
Asp Tyr Asp Ala Lys Asn Ile Val Val Ile Gly Ser Gly Ala Thr Ala
             175                 180                 185 gtc acg ctc gtg ccg gcg ctg gcg gac tcg ggc gcc aag cac gtc acg      809
Val Thr Leu Val Pro Ala Leu Ala Asp Ser Gly Ala Lys His Val Thr
         190                 195                 200 atg ctg cag cgc tca ccc acc tac atc gtg tcg cag cca gac cgg gac      857
Met Leu Gln Arg Ser Pro Thr Tyr Ile Val Ser Gln Pro Asp Arg Asp
     205                 210                 215 ggc atc gcc gag aag ctc aac cgc tgg ctg ccg gag acc atg gcc tac      905
Gly Ile Ala Glu Lys Leu Asn Arg Trp Leu Pro Glu Thr Met Ala Tyr
220                 225                 230                 235 acc gcg gta cgg tgg aag aac gtg ctg cgc cag gcg gcc gtg tac agc      953
Thr Ala Val Arg Trp Lys Asn Val Leu Arg Gln Ala Ala Val Tyr Ser
                 240                 245                 250 gcc tgc cag aag tgg cca cgg cgc atg cgg aag atg ttc ctg agc ctg     1001
Ala Cys Gln Lys Trp Pro Arg Arg Met Arg Lys Met Phe Leu Ser Leu
             255                 260                 265 atc cag cgc cag cta ccc gag ggg tac gac gtg cga aag cac ttc ggc     1049
Ile Gln Arg Gln Leu Pro Glu Gly Tyr Asp Val Arg Lys His Phe Gly
         270                 275                 280 ccg cac tac aac ccc tgg gac cag cga ttg tgc ttg gtg ccc aac ggc     1097
Pro His Tyr Asn Pro Trp Asp Gln Arg Leu Cys Leu Val Pro Asn Gly
     285                 290                 295
```

-continued

```
gac ctg ttc cgg gcc att cgt cac ggg aag gtc gag gtg gtc acc gac    1145
Asp Leu Phe Arg Ala Ile Arg His Gly Lys Val Glu Val Val Thr Asp
300                 305                 310                 315 acc att gaa cgg ttc acc gcg acc gga atc cgg ctg aac tca ggt cgc    1193
Thr Ile Glu Arg Phe Thr Ala Thr Gly Ile Arg Leu Asn Ser Gly Arg
            320                 325                 330 gaa ctg ccg gct gac atc atc att acc gca acg ggg ttg aac ctg cag    1241
Glu Leu Pro Ala Asp Ile Ile Ile Thr Ala Thr Gly Leu Asn Leu Gln
        335                 340                 345 ctt ttt ggt ggg gcg acg gcg act atc gac gga caa caa gtg gac atc    1289
Leu Phe Gly Gly Ala Thr Ala Thr Ile Asp Gly Gln Gln Val Asp Ile
    350                 355                 360 acc acg acg atg gcc tac aag ggc atg atg ctt tcc ggc atc ccc aac    1337
Thr Thr Thr Met Ala Tyr Lys Gly Met Met Leu Ser Gly Ile Pro Asn
365                 370                 375 atg gcc tac acg gtt ggc tac acc aat gcc tcc tgg acg ctg aag gcc    1385
Met Ala Tyr Thr Val Gly Tyr Thr Asn Ala Ser Trp Thr Leu Lys Ala
380                 385                 390                 395 gac ctg gtg tcg gag ttt gtc tgt cgc ttg ttg aat tac atg gac gac    1433
Asp Leu Val Ser Glu Phe Val Cys Arg Leu Leu Asn Tyr Met Asp Asp
            400                 405                 410 aac ggt ttt gac acc gtg gtc gtc gag cga ccg ggc tca gat gtc gaa    1481
Asn Gly Phe Asp Thr Val Val Val Glu Arg Pro Gly Ser Asp Val Glu
        415                 420                 425 gag cgg ccc ttc atg gag ttc acc cca ggt tac gtg ctg cgc tcg ctg    1529
Glu Arg Pro Phe Met Glu Phe Thr Pro Gly Tyr Val Leu Arg Ser Leu
    430                 435                 440 gac gag ctg ccc aag cag ggt tcg cgt aca ccg tgg cgc ctg aat cag    1577
Asp Glu Leu Pro Lys Gln Gly Ser Arg Thr Pro Trp Arg Leu Asn Gln
445                 450                 455 aac tac cta cgt gac atc cgg ctc atc cgg cgc ggc aag atc gac gac    1625
Asn Tyr Leu Arg Asp Ile Arg Leu Ile Arg Arg Gly Lys Ile Asp Asp
            460                 465                 470                 475 gag ggt ctg cgg ttc gcc aaa agg cct gcc ccg gtg ggg gtt tag        1670
Glu Gly Leu Arg Phe Ala Lys Arg Pro Ala Pro Val Gly Val
        480                 485                 490 ctttagcgac ggtttagcgc cggtttaggc catagtcaga cgacgatgat gccgtcgtcg   1730
tcgctgtagg cgatatcgcc cggaacgaat gtcaccccgc ccagcgtgat tcaacgtcg    1790 cgttctccgg caccggtctt ggtgctcttg cggggattgg tgcccagcgc tttgatgccg   1850
atgtcgatgc cgcgcag                                                   1867

<210> SEQ ID NO 2
<211> LENGTH: 489
<212> TYPE: PRT
<213> ORGANISM: Mycobacterium tuberculosis
<220> FEATURE:
<223> OTHER INFORMATION: wild-type EtaA monooxygenase (Rv3854c, EthA)

<400> SEQUENCE: 2

Met Thr Glu His Leu Asp Val Val Ile Val Gly Ala Gly Ile Ser Gly
1               5                   10                  15

Val Ser Ala Ala Trp His Leu Gln Asp Arg Cys Pro Thr Lys Ser Tyr
            20                  25                  30

Ala Ile Leu Glu Lys Arg Glu Ser Met Gly Gly Thr Trp Asp Leu Phe
        35                  40                  45

Arg Tyr Pro Gly Ile Arg Ser Asp Ser Asp Met Tyr Thr Leu Gly Phe

-continued

Arg Phe Arg Pro Trp Thr Gly Arg Gln Ala Ile Ala Asp Gly Lys Pro
65                  70                  75                  80

Ile Leu Glu Tyr Val Lys Ser Thr Ala Ala Met Tyr Gly Ile Asp Arg
            85                  90                  95

His Ile Arg Phe His His Lys Val Ile Ser Ala Asp Trp Ser Thr Ala
        100                 105                 110

Glu Asn Arg Trp Thr Val His Ile Gln Ser His Gly Thr Leu Ser Ala
        115                 120                 125

Leu Thr Cys Glu Phe Leu Phe Leu Cys Ser Gly Tyr Tyr Asn Tyr Asp
    130                 135                 140

Glu Gly Tyr Ser Pro Arg Phe Ala Gly Ser Glu Asp Phe Val Gly Pro
145                 150                 155                 160

Ile Ile His Pro Gln His Trp Pro Glu Asp Leu Asp Tyr Asp Ala Lys
                165                 170                 175

Asn Ile Val Val Ile Gly Ser Gly Ala Thr Ala Val Thr Leu Val Pro
            180                 185                 190

Ala Leu Ala Asp Ser Gly Ala Lys His Val Thr Met Leu Gln Arg Ser
        195                 200                 205

Pro Thr Tyr Ile Val Ser Gln Pro Asp Arg Asp Gly Ile Ala Glu Lys
210                 215                 220

Leu Asn Arg Trp Leu Pro Glu Thr Met Ala Tyr Thr Ala Val Arg Trp
225                 230                 235                 240

Lys Asn Val Leu Arg Gln Ala Ala Val Tyr Ser Ala Cys Gln Lys Trp
                245                 250                 255

Pro Arg Arg Met Arg Lys Met Phe Leu Ser Leu Ile Gln Arg Gln Leu
            260                 265                 270

Pro Glu Gly Tyr Asp Val Arg Lys His Phe Gly Pro His Tyr Asn Pro
        275                 280                 285

Trp Asp Gln Arg Leu Cys Leu Val Pro Asn Gly Asp Leu Phe Arg Ala
    290                 295                 300

Ile Arg His Gly Lys Val Glu Val Thr Asp Thr Ile Glu Arg Phe
305                 310                 315                 320

Thr Ala Thr Gly Ile Arg Leu Asn Ser Gly Arg Glu Leu Pro Ala Asp
                325                 330                 335

Ile Ile Ile Thr Ala Thr Gly Leu Asn Leu Gln Leu Phe Gly Gly Ala
            340                 345                 350

Thr Ala Thr Ile Asp Gly Gln Gln Val Asp Ile Thr Thr Thr Met Ala
        355                 360                 365

Tyr Lys Gly Met Met Leu Ser Gly Ile Pro Asn Met Ala Tyr Thr Val
    370                 375                 380

Gly Tyr Thr Asn Ala Ser Trp Thr Leu Lys Ala Asp Leu Val Ser Glu
385                 390                 395                 400

Phe Val Cys Arg Leu Leu Asn Tyr Met Asp Asp Asn Gly Phe Asp Thr
                405                 410                 415

Val Val Val Glu Arg Pro Gly Ser Asp Val Glu Glu Arg Pro Phe Met
            420                 425                 430

Glu Phe Thr Pro Gly Tyr Val Leu Arg Ser Leu Asp Glu Leu Pro Lys
        435                 440                 445

Gln Gly Ser Arg Thr Pro Trp Arg Leu Asn Gln Asn Tyr Leu Arg Asp
    450                 455                 460

Ile Arg Leu Ile Arg Arg Gly Lys Ile Asp Asp Glu Gly Leu Arg Phe
465                 470                 475                 480

Ala Lys Arg Pro Ala Pro Val Gly Val

485

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:EtaA PCR
      amplification primer

<400> SEQUENCE: 3
ggggtaccga cattacgttg atagcgtgga                                    30

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:EtaA PCR
      amplification primer

<400> SEQUENCE: 4
ataagaatgc ggccgcaacc gtcgctaaag ctaaacc                            37

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 5
atcatccatc cgcagcac                                                 18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 6
aagctgcagg ttcaacc                                                  17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 7
gcatcgtgac gtgcttg                                                  17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 8
aagctgcagg ttcaacc                                                  17

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 9
tgaactcagg tcgcgaac                                                    18

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 10
aacatcgtcg tgatcgg                                                     17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 11
atttgttccg ttatccc                                                     17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 12
aacctagcgt gtacatg                                                     17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 13
tctatttccc atccaag                                                     17

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:EtaA Primer
      3 sequencing primer, EtaA amplification primer

<400> SEQUENCE: 14
gccatgtcgg cttgattg                                                    18

```
<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:EtaR PCR
      amplification primer

<400> SEQUENCE: 15
ggggtaccgc acactatcga cacgtagtaa gc                                    32

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence:EtaR PCR
      amplification primer

<400> SEQUENCE: 16
ataagaatgc ggccgcgcgg ttctcgccgt aaatgct                               37
```

US 7,547,519 B2

METHODS OF DIAGNOSING MULTIDRUG RESISTANT TUBERCULOSIS

CROSS-REFERENCES TO RELATED APPLICATIONS

This application is a divisional of U.S. patent application Ser. No. 09/888,320, filed Jun. 22, 2001, which claims priority to U.S. Provisional Application No. 60/214,187, filed Jun. 26, 2000. The contents of both of these applications are incorporated by reference for all purposes.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The World Health Organization ("WHO") estimates that as much as one-third of the world's population is infected with tuberculosis. In 1998, the latest year for which estimates are available, *Mycobacterium tuberculosis* ("MTb") infected 7.25 million people and resulted in 2.9 million fatalities (Farmer, P. et al., *Int J Tuberc Lung Dis* 2:869 (1998)). Underlying these statistics is an emerging epidemic of multiple drug-resistant ("MDR") tuberculosis that severely undermines control efforts and is transmitted indiscriminately across national borders (Viskum, K. et al., *Int J Tuberc Lung Dis* 1:299 (1997); Bass, J. B. et al., *Am J Respir Crit Care Med* 149:1359 (1994)). Resistance to any of the front-line drugs generally bodes poorly for the patient, who then is committed to a regimen of less active "second-line" therapies. Where multidrug resistance is suspected, the WHO recommends that three or more drugs be administered at the same time, to decrease the chance that the organism will be able to develop resistance to all of the agents.

One of the most efficacious of the second-line drugs is the thioamide ethionamide (ETA) (Farmer, P. et al., supra). Like the front-line drug, isoniazid (INH), ETA is specific for *mycobacteria* and is thought to exert a toxic effect on mycolic acid constituents of the cell wall of the *bacillus* (Rist, N. *Adv Tuberc Res* 10:69 (1960); Banerjee, A. et al., *Science* 263:227 (1994)). Current tuberculosis therapies include a large number of "prodrugs" that must be metabolically activated to manifest their toxicity upon specific cellular targets (Barry, C. B., III et al., *Biochem Pharm* 59:221 (2000)). The best characterized example of this is the activation of INH by the catalase-peroxidase KatG, generating a reactive form that then inactivates enzymes involved in mycolic acid biosynthesis (Slayden, R. A. et al., *Microbes and Infection* (2000) (in press); Heym, B. et al., *Tubercle Lung Dis* 79:191 (1999)). The majority of clinically observed INH resistance is associated with the loss of this activating ability by the *bacillus* (Musser, J. M., *Clin Microbiol Rev* 8:496 (1995)), but such strains typically retain their sensitivity toward ETA, suggesting that ETA activation requires a different enzyme than KatG (Rist, N., *Adv. Tub. Res.* 10, 69 (1960)).

In a striking achievement of molecular biology and genetics, the entire genome of a paradigm *M. tuberculosis* strain, H37Rv (EMBL/GenBank/DDBJ entry AL123456), was sequenced and published in 1998. (Cole, S. et al., Nature 393,537 (1998)). The genome was found to comprise 4,411,531 base pairs, comprising 3,974 putative genes, of which 3,924 were predicted to encode proteins. Each of the putative genes was accorded a number based on its position in the genome relative to a selected start site. The function of many of the putative genes, however, could not be determined when the genome was sequenced and published, and their function remains unknown today.

SUMMARY OF THE INVENTION

The present invention provides methods of determining the ability of a *Mycobacterium tuberculosis* bacterium to oxidize a thioamide or thiocarbonyl, and thereby of determining the resistance of the bacterium to a thioamide or thiocarbonyl drug or prodrug. The methods include, for example, detecting a mutation in the EtaA gene in the bacterium, which a mutation is indicative of decreased ability to oxidize a thioamide or thiocarbonyl. The wild-type sequence of the EtaA gene is set forth in SEQ ID NO:1. Such mutations can include frameshift, missense, and nonsense mutations, as well as single nucleotide polymorphisms (SNPs) which cause amino acid substitutions in the normal sequence encoded by the gene. In particular, the frameshift mutations can include, for example, a deletion at position 65 of the EtaA gene sequence, an addition at position 557, or an addition at position 811. SNPs can result in, for example, any of the following amino acid substitutions: G43C, P51L, D58A, Y84D, T342K, and A381P.

The invention further provides methods of detecting such mutations. These methods include, for example, amplifying the EtaA gene, or a portion thereof containing the mutation, with a set of primers to provide an amplified product, sequencing the amplified product to obtain a sequence, and comparing the sequence of the amplified product with a known sequence of a wild-type EtaA gene, wherein a difference between the sequence of the amplified product and the sequence of the wild-type EtaA gene indicates the presence of a mutation. The amplification can be by any of a variety of techniques, such as PCR. For example, the EtaA gene or a portion thereof can be amplified, the amplified product can be subjected to digestion by restriction enzymes, the resulting restriction products can be separated to form a pattern of restriction fragment lengths, and the pattern of restriction fragment lengths compared to a pattern of restriction fragment lengths formed by subjecting the wild-type EtaA gene (or portion thereof corresponding to the portion of the EtaA gene amplified from the organism being screened) to the same restriction enzymes. The amplification can be by PCR.

In preferred embodiments, the primers for amplifying the gene are selected from the group consisting of 5'-GGGG-TACCGACAT TACGTTGATAGCGTGGA-3' (SEQ ID NO:3); 5'-ATAAGAATGCGGCCGC AAC-CGTCGCTAAAGCTAAACC-3' (SEQ ID NO:4), 5' ATCATCCATCCGCAGCAC 3' (SEQ ID NO:5); 5' AAGCT-GCAGGTTCAACC 3' (SEQ ID NO:6); 5' GCATCGT-GACGTGCTTG 3' (SEQ ID NO:7); 5' AAGCTGCAG GTTCAACC 3' (SEQ ID NO:8); 5' TGAACTCAGGTCGC-GAAC 3' (SEQ ID NO:9); 5' AACATCGTCGTGATCGG 3' (SEQ ID NO:10); 5' ATTTGTTCCGTTATCCC 3' (SEQ ID NO: 11); 5' AACCTAGCGTGTACATG 3' (SEQ ID NO: 12); 5' TCTATTTCCCATCCAAG 3 (SEQ ID NO:13); and 5' GCCATGTCGGCTTGATTG 3' (SEQ ID NO:14). In particularly preferred embodiments, the primers are the sequences of SEQ ID NO:3 and SEQ ID NO:4. The separation of the restriction length fragments can be by gel electrophoresis. An EtaA gene with a known mutation, such as the particular mutated EtaA genes described above, can also be amplified and subjected to restriction enzymes, and the resulting patterns compared to that of a EtaA gene obtained from a biological sample (for example, from a patient) to determine whether the EtaA gene from the biological sample has the same mutation as that of the EtaA gene with the known mutation.

The mutations can also be detected by hybridization techniques. Conveniently, the sample nucleic acid is hybridized to a nucleic acid of known sequence, such as the wild-type EtaA gene or a portion thereof, or to a portion of the gene containing the mutation, under conditions sufficiently stringent that, if the reference nucleic acid is the wild-type sequence, failure of the sample to hybridize to the reference nucleic acid will indicate that it contains a mutation whereas hybridization will indicate it comprises the wild-type sequence. The converse will be true if the reference nucleic acid comprises a mutation. Either the sample nucleic acid or the reference nucleic acid can be immobilized on a solid support.

The mutations can further be detected by detecting mutations in the gene product. This can be accomplished, for example, by specifically binding any of a number of antibodies, such as a single chain Fv portion of an antibody or an antibody fragment which retains antibody recognition, to a gene product with a mutation, wherein such binding is indicative of a mutation indicating that the organism containing the mutation has decreased ability to oxidize a thioamide or thiocarbonyl drug or prodrug compared to an organism bearing a wild-type EtaA gene. Conveniently, the detection of specific binding of the antibody and the gene product can be measured in an ELISA. Mutations can also be detected by mass spectrometry. In another embodiment, the mutation is detected by culturing the organism in the presence of ethionamide and testing for the presence or absence of (2-ethyl-pyridin-4-yl) methanol, wherein the absence of (2-ethyl-pyridin-4-yl) methanol indicates that the bacterium has a mutation which is indicative of decreased ability to oxidize a thioamide. Conveniently, the ethionamide may be radiolabeled.

The invention further provides methods for screening an individual with tuberculosis for the presence of a *M. tuberculosis* bacterium resistant to treatment with a thioamide or a thiocarbonyl drug, comprising obtaining a biological sample containing the bacterium and detecting a mutation in an EtaA gene in the bacterium, wherein detecting the presence of a mutation is indicative the bacterium is resistant to treatment by a thioamide or a thiocarbonyl drug or prodrug. The method can include detecting the mutation by amplification of the EtaA gene with a set of primers to obtain a sequence, sequencing the amplified product, and comparing the sequence to that of the wild-type EtaA gene, SEQ ID NO:1, wherein a difference between the sequence of the amplified product and of the sequence of the wild-type gene indicates the presence of a mutation.

The invention further provides kits for determining the ability of an *M. tuberculosis* organism to oxidize a thioamide or thiocarbonyl. Such kits include a container and appropriate primers for amplifying an EtaA gene or a portion thereof, and may further comprise one or more restriction enzymes. In preferred embodiments, the primers for amplifying the gene are selected from the group consisting of 5'-GGGGTAC-CGACAT TACGTTGATAGCGTGGA-3' (SEQ ID NO:3); 5'-ATAAGAATGCGGCCGC AAC-CGTCGCTAAAGCTAAACC-3' (SEQ ID NO:4), 5' ATCATCCATCCGCAGCAC 3' (SEQ ID NO:5); 5' AAGCT-GCAGGTTCAACC 3' (SEQ ID NO:6); 5' GCATCGT-GACGTGCTTG 3' (SEQ ID NO:7); 5' AAGCTGCAG GTTCAACC 3' (SEQ ID NO:8); 5' TGAACTCAGGTCGC-GAAC 3' (SEQ ID NO:9); 5' AACATCGTCGTGATCGG 3' (SEQ ID NO:10); 5' ATTTGTTCCGTTATCCC 3' (SEQ ID NO:11); 5' AACCTAGCGTGTACATG 3' (SEQ ID NO:12); 5' TCTATTTCCCATCCAAG 3 (SEQ ID NO:13); and 5' GCCATGTCGGCTTGATTG 3' (SEQ ID NO:14). In particularly preferred embodiments, the primers are the sequences of SEQ ID NO:3 and SEQ ID NO:4. An EtaA gene with a known mutation can also be included as a positive control.

In other embodiments, the kits may provide materials for performing ELISA or immunoassays to detect organisms with decreased ability to oxidize thioamides, or to detect products of thioamide metabolism. The kits may also contain radiolabeled ethionamide to permit detection of labeled metabolic products in the presence of an organism which can metabolize the drug. Moreover, the kits may contain materials for performing thin-layer chromatography, and may contain (2-ethyl-pyridin-4-yl)methanol for use as a positive control. Alternatively, or in addition, the kits may include an antibody that binds to a product of the EtaA gene or to (2-ethyl-pyridin-4-yl)methanol. The kits may also contain instructions for detecting mutations in the EtaA gene, such as the specific mutations identified above. Detection of such mutations indicates that the organism has decreased ability to oxidize a thioamide.

BRIEF DESCRIPTION OF THE DRAWINGS

FIG. 1A. Metabolism of radiolabeled ETA by MTb. Lanes a-h correspond to sequential supernatant samples taken at times: 0.2, 0.25, 0.75, 1.5, 5.0, 8.5, and 25 hours, respectively. Lane i represents media autooxidation following 25 hr of incubation without bacterial cells. These metabolites correspond to ETA S-oxide (2), ETA nitrile (3) and ETA amide (4)

FIG. 1B. Cell associated radioactivity counts graphed against time. "DPM," disintergrations per minute.

FIG. 1C. Left graph. The unknown major metabolite (5) was confirmed as (2-ethyl-pyridin-4-yl)methanol by co-chromatography with a synthetic characterized alcohol standard. Right hand graphs. Upper panel: HPLC continuous radiodetector spectrum corresponds to FIG. 1A. lane i, media control. Lower panel: HPLC continuous radiodetector spectrum corresponds to FIG. 1A, lane d, time point 1.5 hr, where the UV254 trace of (2-ethyl-pyridin-4-yl)methanol is superimposed FIG. 2. EtaA and EtaR control ETA susceptibility and metabolism. Photographs of MSm pMH29 *mycobacteria* clones grown on 7H11 plates containing the indicated concentration of drugs. "Control" indicates no drug added. "INF 12.5" indicates isoniazid was present at 12.5 μg/ml. "ETA 2.5, 12.5, and 62.5" indicate that ethionamide was present at the μg/ml indicated. Within each photograph, the vertical columns show MSm clones which were tranformed with EtaA (a); vector control (b); or EtaR (c), respectively, and spotted in 10-fold dilutions (from top to bottom).

FIG. 3A. The MSm clones shown in FIG. 2 were analyzed for their ability to metabolize [1-$^{14}$C]ETA. Lanes a-f correspond to samples taken at times: 0, 30, 90, 180, 330 and 900 minutes, respectively. Metabolites were identified as in FIG. 1.

FIG. 3B. Cell-associated radioactivity was determined as in FIG. 1B. "DPM," disintegrations per minute. Squares represent MSm overexpressing EtaA, circles represent wild type MSm, triangles represent MSm overexpressing EtaR.

FIG. 3C. Macromolecule-associated radioactivity. "DPM," disintegrations per minute. Columns 1, 2, and 3 show counts for MSm overexpressing EtaA, wild type MSm, and MSm overexpressing EtaR, respectively.

FIG. 4A. Thiacetazone (1) and thiocarlide (2).

FIG. 4B. Map of mutations in EtaA found in patient isolates resistant to ETA and thiacetazone. Chromosome coordinates and gene designations are in reference to the sequenced genome of MTb strain H37Rv. The "811" and "65" above the arrow denote nucleotide positions within the gene sequence. The notations "+1 nt" and "Δ1 nt" below the arrow denote that the patient isolate was found to have a nucleotide added or deleted, respectively, at the position indicated. The other notations below the arrow for the EtaA gene denote, in standard single letter code, substitutions at positions in the amino acid sequence of the gene product.

FIG. 4C. Cross-resistance determination of patient isolates and the associated nucleotide alterations observed. The individual patient isolates are listed vertically in the column entitled "Strain." The final entry in that column is a mono-resistant strain of MTb (ATCC 35830) obtained from the American Type Culture Collection (Manassas, Va.). The next four columns set forth the observed growth of the isolate when cultured with the indicated drug. ETA: ethionamide, TA: thiacetazone, TC: thiocarlide, INH: isoniazid. Susceptibility to ETA is reported as follows: S: susceptible (if the culture failed to grow at 2.5 μg/ml), L: low-level resistance (if weak growth was observed at 2.5 μg/ml), M: moderate resistance (if strong growth was observed at 2.5 μg/ml), and H: high-level resistance (if growth was observed at 10 μg/ml). Susceptibility to TA/TC/INH is reported as follows: S: susceptible (if the culture failed to grow at 0.5 μg/ml), L: low-level resistance (if weak growth was observed at 0.5 μg/ml), M: moderate resistance (if weak growth was observed at 2.0 μg/ml), and H: high-level resistance (if strong growth was observed at concentrations greater than 2.0 μg/ml). The column titled "Nucleotide" denotes the position in the nucleotide sequence of the gene at which a mutation, if any, was found. The column titled "Amino-acid" indicates whether the nucleotide mutation denoted in the column to its left resulted in an amino acid substitution and, if so, the particular substitution and the position of the affected amino acid in the normal amino acid sequence of the protein encoded by EtaA.

FIG. 5. The sequence of the EtaA gene. The coding region (SEQ ID NO:1) consists of the 1467 numbered nucleotides. Portions of the untranslated 5' and 3' regions are shown.

FIG. 6. The amino acid sequence (SEQ ID NO:2) of the protein encoded by the EtaA gene.

DETAILED DESCRIPTION

Introduction

It has now been discovered that two of the putative genes of *M. tuberculosis*, Rv3854c and Rv3855, regulate the susceptibility of *M. tuberculosis* to the major second-line drug, ethionamide ("ETA"), used to treat tuberculosis. Specifically, it has now been discovered that the gene currently known as Rv3854c is a monooxygenase. Further, it has now been discovered that this gene confers upon *Mycobacteria* the ability to activate thioamide and thiocarbonyl drugs from their pro-drug form to their active drug form. When the tuberculosis genome was sequenced and analyzed in 1998, the gene was considered to bear homology to a bacterial monooxygenase, but was sufficiently different to be classified as a separate, unknown family. Moreover, its substrate was unknown.

It has now further been discovered that the gene currently known as Rv3855 is a regulator of expression of the monooxygenase encoded by Rv3854c, and can repress its expression. In recognition of the discovery of the functions of these genes, we have renamed Rv3854c and Rv3855 as EtaA and EtaR, respectively.

It has further been discovered that mutations in the EtaA gene are diagnostic of resistance to ETA. Analysis of patient isolates revealed a 100% correlation between mutations in this gene and resistance to ETA. When resistance was selected for, both frameshift mutations, consisting of the deletion or addition of a single nucleotide, and single nucleotide polymorphisms ("SNPs") which resulted in the substitution of one amino acid residue for another, resulted in an ETA-resistant phenotype. It has previously been recognized that *M. tuberculosis* has an extremely low rate of synonymous mutations; that is, the organism has few if any random mutations which do not have a functional effect. E.g., Sreevatsan, S., et al. Proc Natl Acad Sci USA 94(18):9869-74 (1997). Accordingly, it is expected that any mutation in this gene, whether frameshift, nonsense, missense, or SNP, will result in an ETA-resistant phenotype. The Examples show that all the mutations studied, including two frameshift mutations and seven SNPs, resulted in increased resistance to ETA. By contrast, three isolates selected for by resistance to thioacetazone which were not also cross resistant to ETA, and the wild-type strain which showed an ETA-sensitive phenotype, were mutation free in the EtaA/EtaR and intergenic regions. The knowledge of the EtaA gene sequence and of the function of the gene permits one of skill in the art to readily identify any particular mutation of the EtaA gene in an ETA-resistant organism.

It has further been discovered that organisms with mutations in the EtaA gene are resistant not only to ETA, but also to two other thioamide compounds also used as second-line drugs. Thus, mutations in this gene reduce or eliminate the value of at least three of the drugs which have been used in combination therapy for MDR tuberculosis. Based on the present findings, it can also be predicted that organisms with mutations in this gene will be resistant to other thioamide- or thiocarbonyl-based therapeutic agents.

The extensive cross-resistance among these compounds predicts two overlapping mechanisms of resistance: (a) target associated, like the resistance between INH and ETA and (b) activation-associated, like the resistance among ETA (a thioamide), thioacetazone (a thioamide), and thiocarlide (a thiocarbonyl). Such considerations complicate appropriate drug therapy for the treatment of multidrug-resistant tuberculosis and the discovery of the cross-resistance to these compounds provides an important tool to help understand the resistance mechanisms operating in a single patient, which may prove vital to determining appropriate treatment for that patient.

These discoveries permit a much more rapid determination of whether the particular organism infecting a patient is resistant to these second-line agents. Detection of mutations in the EtaA gene can be used to diagnose a phenotype resistant to treatment by ETA, and the other thioamide drugs, thiacetazone and thiocarlide, used as second-line agents. In addition, the knowledge of the pathway by which ETA is metabolized permits diagnosis of a drug-resistant phenotype by detecting differences in the rate of production of end-products or intermediates.

The diagnosis of a phenotype resistant to thioamide drugs has important clinical implications. *M. tuberculosis* tends to develop resistance to drugs when used as single agents ("monotherapy"). Drug-resistant tuberculosis is therefore generally treated with at least two and preferably three different agents, since it is less likely that the organism will be able to develop resistance to all three of the agents simultaneously. ETA is one of the most important drugs recommended by the World Health Organization for use in the case of multidrug resistant ("MDR") strains of tuberculosis. If a patient with MDR tuberculosis has a mutation of EtaA rendering the patient resistant to thioamide therapies, however, the ETA will have limited or no effect, and it will be as if the patient has been administered only one or only two agents. The chance that the *M. tuberculosis* strain present in the patient will develop resistance to the other agents is thus higher than expected and, if such resistance develops, no drugs may be left which are capable of effectively combating the organism.

Figure 1:
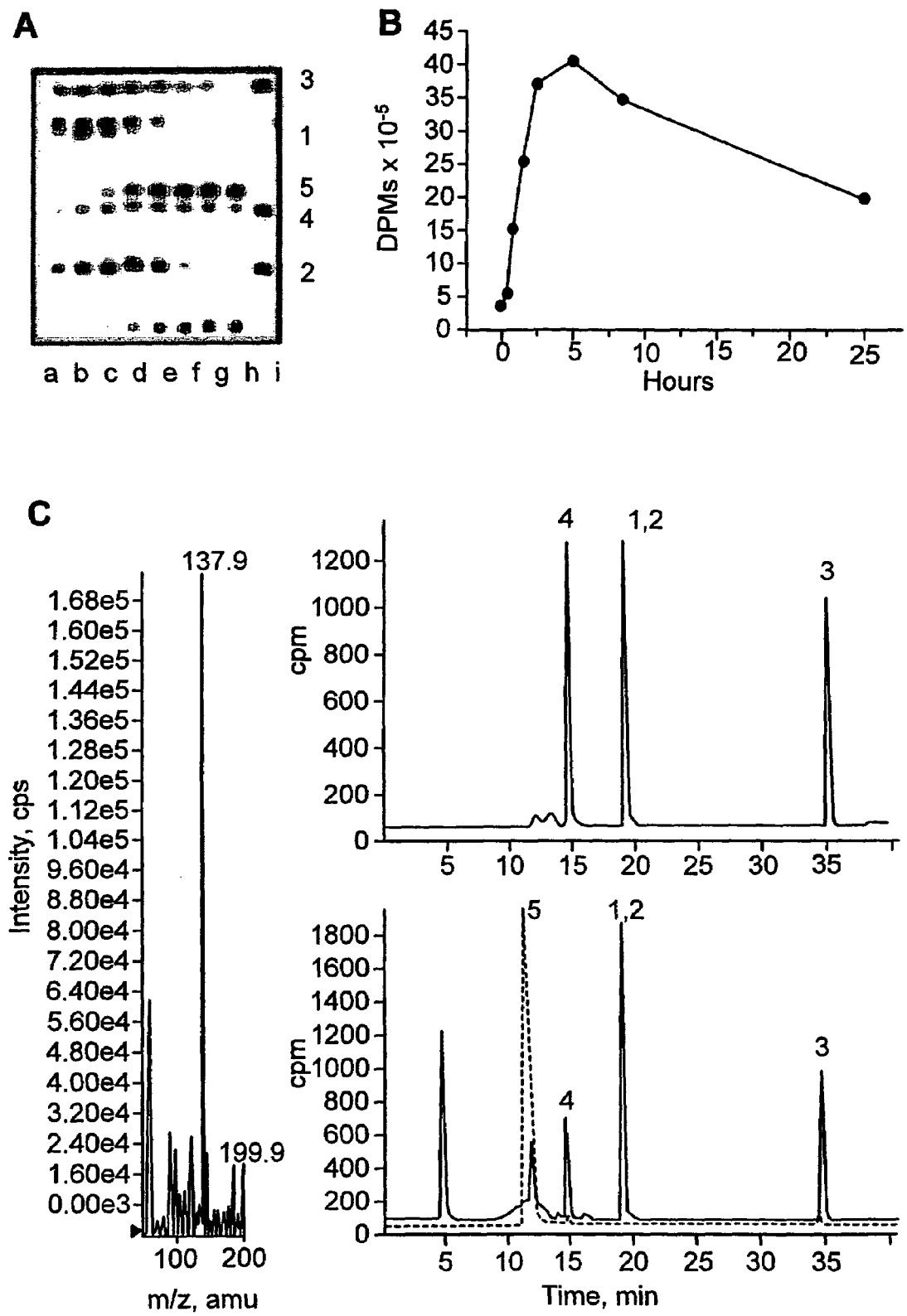
FIG. 1. In vivo production of (2-ethyl-pyridin-4-yl)methanol (5) from ETA by whole cells of MTb.
Figure 2:
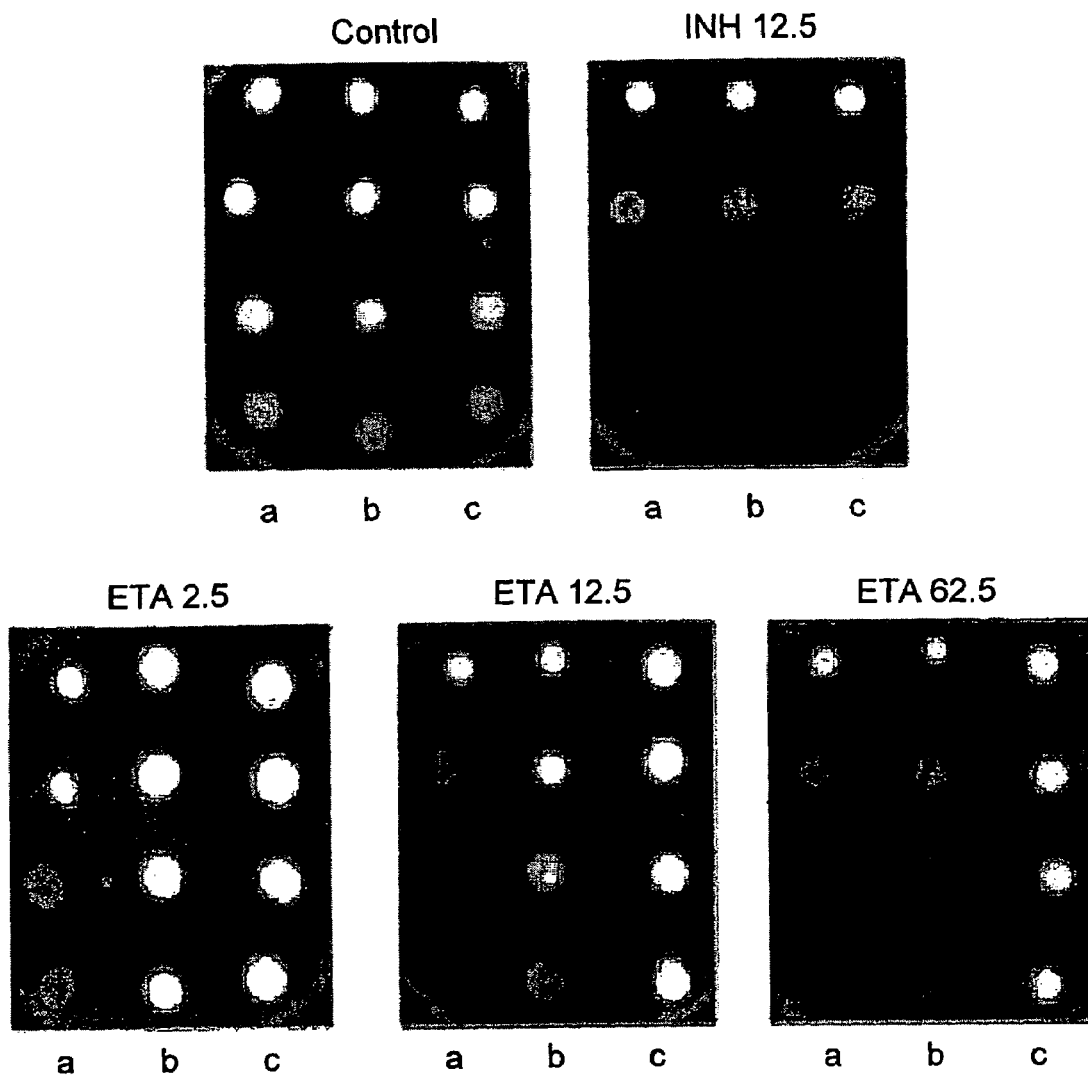
Figure 3:
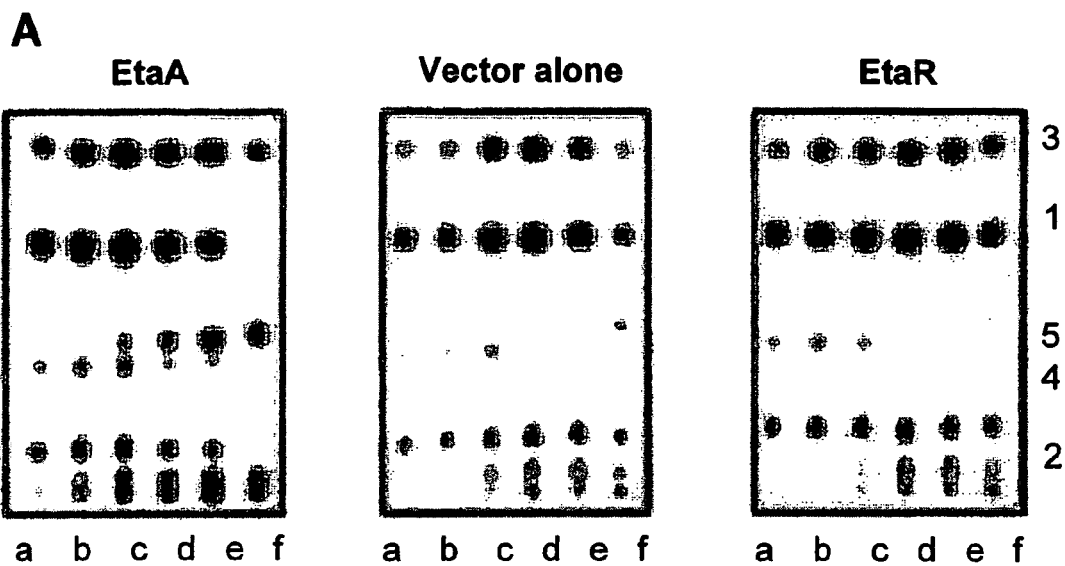
FIG. 3.
Figure 3:
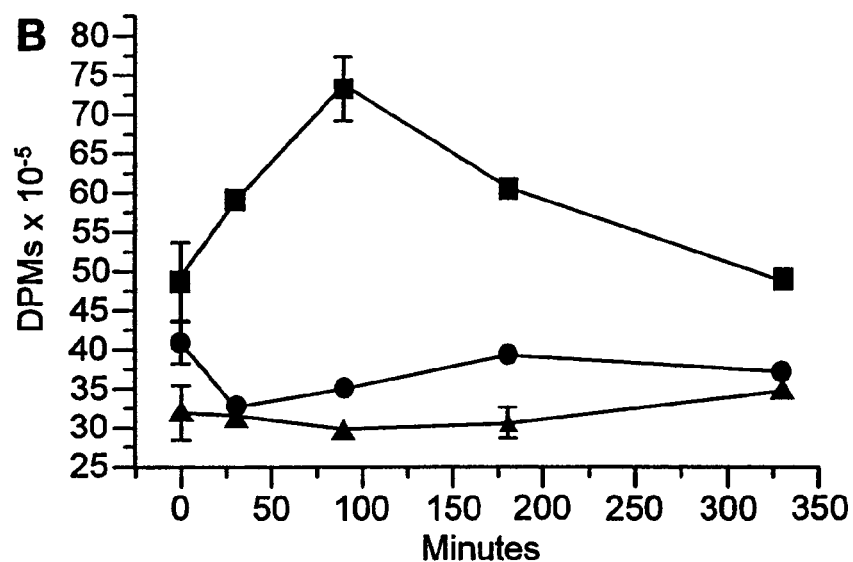
Figure 3:
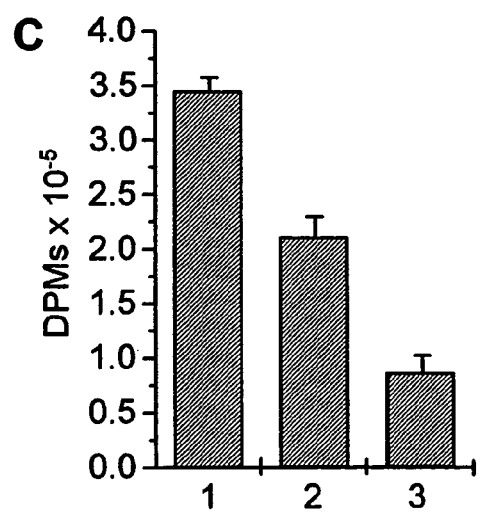
Figure 4:
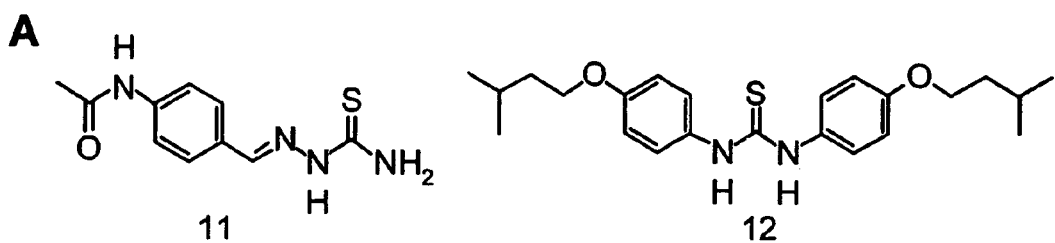
FIG. 4. EtaA and EtaR associated mutations and cross-resistance in patient isolates from Cape Town, South Africa.
Figure 4:
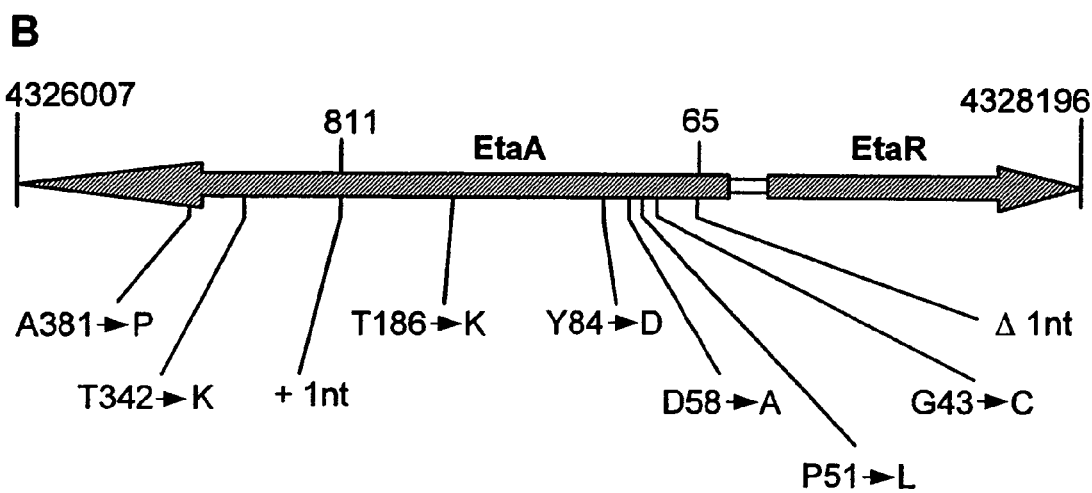

Additionally, mutations in the EtaA gene permit rapid identification of MDR organisms by PCR and other techniques, rather than by having to culture the organisms in the presence of various antibiotics. This is especially useful because *Mycobacteria* are such slow growers that patients not infrequently die before the *Mycobacteria* infecting them can be cultured and their susceptibility determined by conventional means. The rapid identification of organisms permitted by the invention reduces this problem, and also permits more rapid monitoring of possible nosocomial spread. Additionally, the prompt confirmation or exclusion of possible transmission allows early clinical intervention to prevent or reduce future outbreaks of MDR-tuberculosis.

Definitions and Terms

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

Residues mutated from a known sequence are designated by convention by listing in standard single letter code the residue normally found at a designated position in the sequence, the position in the sequence of the residue mutated, and the residue substituted for the original residue. Thus, for example, "G43C" or "G43→C" indicates that a glycine residue normally found at position 43 of the relevant sequence has been replaced or substituted by a cysteine.

References here to "MTb" refer to *Mycobacterium tuberculosis*. The sequence of the entire genome of MTb is set forth in TubercuList, found on the internet by entering "http://" followed by "genolist.pasteur.fr/TubercuList/".

References herein to "Rv3854c" and "EtaA" are to a gene found in MTb and designated as Accession Number Rv3854c in TubercuList at the web site noted above. The EtaA gene is also designated as "EthA". As used herein, the term "wild-type EtaA gene" and references to the EtaA gene or EthA gene without further elaboration refer to the sequence set forth in TubercuList under Accession Number Rv3854c. The gene has 1467 base pairs and has the following coordinates in the published *M. tuberculosis* genome: 4326007 and 4327473. TubercuList lists the gene as encoding a 489 amino acid monooxygenase with a molecular weight of 55329.2 and a pI of 8.3315. The published sequences of the EtaA (EthA) gene and of the protein encoded by the gene are set forth as SEQ ID NO:1 and SEQ ID NO:2, respectively.

The gene described herein as "EtaR" is also designated as "EthR." It is available in TubercuList under accession number Rv3855.

As used herein, "antibody" includes reference to an immunoglobulin molecule immunologically reactive with a particular antigen, and includes where appropriate both polyclonal and monoclonal antibodies. The term also includes genetically engineered forms such as chimeric antibodies (e.g., humanized murine antibodies), heteroconjugate antibodies (e.g., bispecific antibodies). The term particularly refers herein to recombinant single chain Fv fragments (scFv), disulfide stabilized (dspv) Fv fragments, or pFv fragments. The term "antibody" also includes antigen binding forms of antibodies, including fragments with antigen-binding capability (e.g., Fab', $F(ab')_2$, Fab, Fv and rIgG. See also, Pierce Catalog and Handbook, 1994-1995 (Pierce Chemical Co., Rockford, Ill.); Kuby, J., *Immunology,* 3rd Ed., W.H. Freeman & Co., New York (1998). Which particular sense or senses of the term are intended will be clear in context.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

The terms "stringent hybridization conditions" or "stringent conditions" refer to conditions under which a nucleic acid sequence will hybridize to its complement, but not to other sequences in any significant degree. Stringent conditions in the context of nucleic acid hybridizations are sequence dependent and are different under different environmental parameters. Longer sequences hybridize specifically at higher temperatures. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays," Elsevier, New York, (1993) (the entirety of Tijssen is hereby incorporated by reference). Very stringent conditions are selected to be equal to the $T_M$ point for a particular probe. Less stringent conditions, by contrast, are those in which a nucleic acid sequence will bind to imperfectly matched sequences. Stringency can be controlled by changing temperature, salt concentration, the presence of organic compounds, such as formamide or DMSO, or all of these. The effects of changing these parameters are well known in the art. The effect on $T_m$ of changes in the concentration of formamide, for example, is reduced to the following equation: $T_m$=81.5+16.6 (log $Na^+$)+0.41 (% G+C)−(600/oligo length)−0.63(% formamide). Reductions in Tm due to TMAC and the effects of changing salt concentrations are also well known. Changes in the temperature are generally a preferred means of controlling stringency for convenience, ease of control, and reversibility. Exemplary stringent conditions for detecting single nucleotide polymorphisms are set forth in numerous references, including Winichagoon, et al. Prenat Diagn 19:428-35 (1999); Labuda et al., Anal Biochem 275:84-92 (1999); and Bradley et al., Genet Test 2:337-41 (1998).

"Solid support" and "support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Detecting Mutations in the EtaA Gene

As noted in the Introduction, MTb is known to have an extremely low rate of "synonymous" mutations; that is, MTh rarely has random mutations that do not affect the function of the organism. Thus, any mutation in the EtaA gene is expected to alter the gene sufficiently so that the enzyme encoded by the gene has reduced ability to activate a thioamide prodrug. Thus, any mutation in the EtaA gene carried by an MTb *bacillus* is indicative of that that organism is resistant to therapy by thioamide drugs and, in particular, to the thioamide drugs ETA, thiacetazone, and thiocarlide.

There are a number of methods known in the art for detecting mutations in a given gene. Mutations in the gene can be found directly by amplifying the gene in a MTb of interest and comparing the sequence of the organism's gene to that of a reference EtaA gene sequence, such as the one set forth in TubercuList. Alternatively, one can digest samples of the EtaA gene of the organism of interest (such as that of a MTb isolated from a patient) and of a known ETA-susceptible MTb organism with restriction enzymes, separate the resulting fragments by electrophoretic techniques routine in the art (such as those taught in *Current Protocols in Molecular Biology*, F. M. Ausubel et al., eds., Current Protocols, Greene Publishing Associates, Inc./John Wiley & Sons, Inc., (1994 Supplement) ("Ausubel")), and compare the pattern of the fragments, with a difference in the pattern of the fragments of the sample compared to that of the EtaA-susceptible organism being indicative of an impaired ability of the organism to metabolize ETA. This method, known as "restriction fragment length polymorphism," or "RFLP," is well known in the art.

The nature of the mutation can be determined by, for example, sequencing the gene isolated from the individual organism. If the specific mutation found is not one already identified as resulting in impaired ability of the enzyme expressed from the gene, the mutation can be tested by any of a variety of standard methods to determine the effect of the mutation. For example, the gene can be transformed into a species of *Mycobacteria* known to be somewhat resistant to Eta compared to wild-type (H37Rv), the gene expressed, and the activity of the resulting enzyme compared for activity against the enzyme expressed by identical cells transformed with a wild-type EtaA gene. An exemplary assay for transforming cells and determining the activity of the EtaA enzyme is set forth in the Examples herein.

Another method known in the art is "CFLP," or "cleavase fragment length polymorphism." This method involves amplifying the gene of interest, here EtaA, followed by digestion with cleavase I, which cuts the DNA at sites dependent on secondary structure. Results are resolved on agarose gels, forming a "bar code"—like pattern which is indicative of the particular gene. Different patterns of cleavage digestion products are obtained for wild-type and mutant samples. The technique is sensitive enough to detect mutations as subtle as point mutations.

Single-stranded conformation polymorphism ("SSCP") has been used to identify a number of different drug resistant phenotypes in selected organisms." Line hybridization assays permit identification of mutant forms of genes responsible for resistance after amplification of relevant genes by the hybridization patterns of probes to samples. Resistance can be determined, for example, by reverse hybridization line probe assay, or "LiPA." Kits for assays for several genes, such as various mutations in the cystic fibrosis gene, are available commercially from Innogenetics N.V. (Zwijnaarde, Belgium). For example, in the HLA typing assay, amplified biotinylated DNA is chemically denatured, and the single strands are hybridized with specific oligonucleotide probes immobilized as parallel lines on membrane-based strips. Then, strepavidin labeled with alkaline phosphatase is added and bound to any biotinylated hybrid previously formed. Incubation with an appropriate substrate results in a precipitate, and the reactivity of the probes can be determined.

A further method known in the art is temperature modulation heteroduplex chromatography ("TMHC"). The method involves amplification of the gene of interest, here the EtaA gene, followed by denaturing of the PCR products and then slowly cooling, to a predetermined temperature based on the composition of the sample. While cooling, the PCR products renature forming hetero and homoduplexes which are resolved from one another using TMHC. Conveniently, the resolution is performed using a WAVE® DNA fragment analysis system (Transgenomic, Inc., San Jose, Calif.).

In another set of embodiments, mutations in the EtaA gene are detected by hybridizing the gene or portions thereof from a biological sample, such as from an individual, against a reference nucleic acid, such as the wild-type EtaA gene or one or more EtaA genes with a known mutation (for ease of discussion herein, the reference nucleic acids will be termed "probes" and the sample being screened the "nucleic acid of interest"). The hybridizations can be performed while either the probes or the nucleic acids of interest are attached to solid supports, or while they are in a fluid environment.

In one set of embodiments, the hybridizations are performed on a solid support. For example, the nucleic acids of interest (or "samples") can be spotted onto a surface. Conveniently, the spots are placed in an ordered pattern, or array, and the placement of where the nucleic acids are spotted on the array is recorded to facilitate later correlation of results. The probes are then hybridized to the array. Conversely, the probes can be spotted onto the surface to form an array and the samples hybridized to that array. In another set of embodiments, beads are used as solid supports. Conveniently, the beads can be magnetic or made of materials responsive to magnetic force, permitting the beads to be moved or separated from other materials by externally applied magnetic fields.

The composition of the solid support can be anything to which nucleic acids can be attached. It is preferred if the attachment is covalent. The material for the support for use in any particular instance should be chosen so as not to interfere with the labeling system to be used for the probes or the nucleic acids. For example, if the nucleic acids are labeled with fluorescent labels, the material chosen for the support should not be one which fluoresces at wavelengths which would interfere with reading the fluorescence of the labels.

Preferably, the support is of a material to which the samples and probes bind or one which is substantially non-porous to them, so that the oligonucleotides remain accessible (i.e., to the probes or the samples) at the surface of the support. Membranes porous to the nucleic acids may be used so long as the membrane can bind sufficient amounts of nucleic acid to permit the hybridization procedures to proceed. Suitable materials should have chemistries compatible with oligonucleotide attachment and hybridization, as well as the intended label, and include, but are not limited to, resins, polysaccharides, silica or silica-based materials, glass and functionalized glass, modified silicon, carbon, metals, nylon, natural and synthetic fibers, such as wool and cotton, and polymers.

In some embodiments, the solid support has reactive groups such as carboxy- amino- or hydroxy groups to facilitate attachment of the oligonucleotides (that is, the samples or the probes). Plastics may be used if modified to accept attachment of nucleic acids or oligonucleotides (since plastic usually has innate fluorescence, the use of non-fluorescent labels is preferred for use with plastic substrates. If plastic materials are used with fluorescent labels, appropriate adjustments should be made to procedures or equipment, such as the use of color filters, to reduce any interference in detecting results due to the fluorescence of the substrate). Polymers may include, e.g., polystyrene, polyethylene glycol tetraphtalate, polyvinyl acetate, polyvinyl chloride, polyvinyl pyrrolidone, buty rubber, and polycarbonate. The surface can be in the form of a bead. Means of attaching oligonucleotides to such supports are well known in the art, and are set forth, for example, in U.S. Pat. Nos. 4,973,493 and 4,569,774 and PCT International Publications WO 98/26098 and WO 97/46313. See also, Pon et al., Biotechniques 6:768-775 (1988); Damba, et al., Nuc. Acids Res. 18:3813-3821 (1990).

Alternatively, the samples can be placed in separate wells or chambers and hybridized in their respective well or chambers. The art has developed robotic equipment permitting the automated delivery of reagents to separate reaction chambers, including "chip" and microfluidic techniques, which allow the amount of the reagents used per reaction to be sharply reduced. Chip and microfluidic techniques are taught in, for example, U.S. Pat. No. 5,800,690, Orchid, "Running on Parallel Lines" New Scientist, Oct. 25, 1997, McCormick, et al., *Anal. Chem.* 69:2626-30 (1997), and Turgeon, "The Lab of the Future on CD-ROM?" *Medical Laboratory Management Report.* December 1997, p.1. Automated hybridizations on chips or in a microfluidic environment are contemplated methods of practicing the invention.

Although microfluidic environments are one embodiment of the invention, they are not the only defined spaces suitable for performing hybridizations in a fluid environment. Other such spaces include standard laboratory equipment, such as the wells of microtiter plates, Petri dishes, centrifuge tubes, or the like can be used.

Another method for identifying the presence of SNPs is the oligonucleotide ligation assay ("OLA"), which may conveniently be coupled with flow cytometric analysis for rapid, accurate analysis of SNPs. See, e.g., Iannone, M. A., et al., Cytometry, 39(2):131-40 (2000); and Jinneman, K. C., et al., J. Food Prot. 62(6):682-5 (1999). PCR and OLA can be used in tandem with yet another technique, Sequence-Coded Separation, or "SCS," to provide specificity, sensitivity, and multiplex capability. See, e.g., Brinson, E. C., et al., Genet Test 1(1):61-8 (1997) (erratum in Genet Test 2(4): 385 (1998)).

SNPs are also detected in the art by reverse dot blot allele-specific oligonucleotide (ASO) hybridization. See, e.g., Winichagoon, et al. Prenat Diagn 19:428-35 (1999), and Labuda et al., Anal Biochem 275:84-92 (1999). One method asserted to be faster than ASO hybridization for detecting single base pair changes is the so-called amplification of refractory mutation system, or "ARMS." See, e.g., Bradley et al., Genet Test 2:337-41 (1998).

Mass spectrometry ("MS") can also be used to detect SNPs. For example, matrix-assisted laser desorption-ionization-time-of-flight ("MALDI-TOF") MS has been shown to be adaptable to high-throughput applications for detecting SNPs. See, e.g., Griffin, T., and Smith, L., Trends Biotechnol 18(2):77-84 (2000). A cost effective procedure for identifying SNPs using MS is taught by Sauer, S., et al., Nucl Acids Res 28(5):E13 (March 2000).

In addition to these gene-based techniques, a variety of techniques are available which screen for functional changes, specifically, by screening for inhibition of monooxygenases. E.g., Crespi, C. L., et al., Med. Chem. Res. 8(7/8):457-471 (1998); Crespi, C. L., et al., Anal Biochem 248(1):188-90 (1997). The latter reference provides a fluorescent method for determining the $IC_{50}$ for a test compound and detailed optimizations of the procedure for nine cytochrome P450 enzymes are set forth by GENTEST Corp. (Woburn, Mass.) which can be found on-line by entering "www." followed by "gentest.com". Modification of this procedure for the enzyme encoded by the EtaA gene, using ETA as the substrate, will be readily apparent to persons of skill in the art. In these assays, the enzyme encoded by the wild-type EtaA gene (the "control enzyme") is tested to determine the $IC_{50}$ of ETA. The enzyme encoded by the EtaA gene of a MTb of interest (the "test enzyme"), such as that obtained in a biological sample from a person to be screened, is then tested by the same procedure. A difference in the $IC_{50}$ of the test enzyme compared to that of the control enzyme indicates a mutation in the gene.

Mutations in the gene can also be detected by detecting mutated forms of the protein encoded by the gene. A mutation that results in a truncated protein or one with a conformation other than that of the normal enzyme can be expected to have epitopes which are not present on the normal enzyme. These mutated forms of the enzyme can be used to raise antibodies. Methods of producing polyclonal and monoclonal antibodies are known to those of skill in the art. See, e.g., Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif.; Goding (1986) *Monoclonal Antibodies: Principles and Practice* (2d ed.) Academic Press, New York, N.Y.; Birch and Lennox, *Monoclonal Antibodies: Principles and Applications*, Wiley-Liss, New York, N.Y. (1995). Antibodies so raised are generally tested by being absorbed against the normal enzyme (conveniently, the enzyme is immobilized on a column and the antibodies run over the column) to remove those which cross react with the form of the enzyme expressed by the normal EtaA gene.

In another set of embodiments, mutations in the EtaA gene can be detected by culturing MTb of interest, such as those isolated from a biological sample from a person being screened for resistant MTb, in a medium containing ETA and detecting whether the culture medium does or does not contain a metabolic product indicating that the monooxygenase encoded by the EtaA gene is functional. For example, the tests can detect the metabolic product (2-ethyl-pyridin-4-yl)-methanol, which the results herein establish for the first time is the product of ETA metabolism by susceptible MTb. The presence of this product in the culture medium of MTb cultured with ETA indicates that the organism being tested is susceptible to ETA treatment; the absence of this product in the medium indicates that the organism is resistant. Conveniently, a culture of a reference ETA-susceptible MTb is grown at the same time as a control so that the presence or absence of the metabolic product in the medium of the MTb of interest can be compared to that present in the medium from the control organism. In preferred forms, radiolabeled ETA is used and the presence of the radiolabeled product is detected in the test and reference cultures over a period of time is detected. For example, if $^{14}C$-labeled ETA is added to a culture of *M. tuberculosis*, the subsequent presence of $^{14}C$-labeled (2-ethyl-pyridin-4-yl)-methanol indicates that the organisms are susceptible to ETA.

The presence of the metabolic product can be determined by any of a number of analytic means known in the art. The Example section describes the use of several of these methods, thin-layer chromatography (TLC) high-pressure liquid chromatography(HPLC), and mass spectrometry, to identify (2-ethyl-pyridin-4-yl)-methanol as the major metabolic product of EtaA-encoded monooxygenase activity. Other techniques can, however, also be used to identify this metabolic product, such as raising antibodies to (2-ethyl-pyridin-4-yl)-methanol by the methods discussed above and using the antibodies to quantitate the presence or absence of (2-ethyl-pyridin-4-yl)-methanol in culture media by ELISAs. In a preferred embodiment, the determination is made by subjecting a sample from the culture to TLC in which a sample known to be (2-ethyl-pyridin-4-yl)-methanol is run as a control. Where the ETA has been radioactively labeled, detection of the metabolic product can be by subjecting the TLC to autoradiography. Immunoassays can also employ chemiluminescence or electroluminescence detection systems. Such systems include luminol, isoluminol, acridinium phenyl esters and other acridinium chemiluminophores such as acridinium (N-sulphonyl)carboxamides, and ruthenium salts for the detection of conventional enzyme-labelled conjugates. These agents are typically used in ELISAs or in conjunction with a chemiluminescent substrate.

Methods for Amplification of the EtaA Gene or Portions Thereof

Some of the detection methods discussed above employ amplification of the EtaA gene. The EtaA gene or desired portions thereof can be amplified by cloning or by other in vitro methods, such as the polymerase chain reaction (PCR), the ligase chain reaction (LCR), the transcription-based amplification system (TAS), the self-sustained sequence replication system (SSR). These and other amplification methodologies are well known to persons of skill.

Examples of these techniques and instructions sufficient to direct persons of skill through cloning exercises are found in Berger and Kimmel, *Guide to Molecular Cloning Techniques, Methods in Enzymology* Vol. 152, Academic Press, Inc., San Diego, Calif. (1987) (hereinafter, "Berger"); Sambrook et al., *Molecular Cloning—A Laboratory Manual* (2nd ed.) Vol. 1-3, Cold Spring Harbor Laboratory, Cold Spring Harbor Press, NY (1989), ("Sambrook et al."); Ausubel, supra; Cashion et al., U.S. Pat. No. 5,017,478; and Carr, European Patent No. 0 246 864.

Examples of techniques sufficient to direct persons of skill through other in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) ("Innis"); Arnheim & Levinson (Oct. 1, 1990) *C&EN* 36-47; *J. NIH Res.*, 3: 81-94 (1991); Kwoh et al., *Proc. Natl. Acad. Sci. USA* 86: 1173 (1989); Guatelli et al., *Proc. Natl. Acad. Sci. USA* 87, 1874 (1990); Lomell et al. *J. Clin. Chem.*, 35: 1826 (1989); Landegren et al., *Science*, 241: 1077-1080 (1988); Van Brunt, *Biotechnology*, 8: 291-294 (1990); Wu and Wallace, *Gene*, 4: 560 (1989); and Barringer et al., *Gene*, 89: 117 (1990).

In one preferred embodiment, the MTb EtaA gene can be isolated by routine cloning methods. The cDNA sequence of the gene can be used to provide probes that specifically hybridize to the EtaA gene in a genomic DNA sample (Southern blot), or to the EtaA mRNA, in a total RNA sample (e.g., in a Northern blot), or to cDNA reverse-transcribed from RNA (in a Southern blot)). Once the target EtaA nucleic acid is identified (e.g., in a Southern blot), it can be isolated according to standard methods known to those of skill in the art (see, e.g., Sambrook et al., supra; Berger, supra, or Ausubel, supra).

In another preferred embodiment, the MTb EtaA cDNA can be isolated by amplification methods such as polymerase chain reaction (PCR). One example of amplifying the MTb EtaA gene, including the primers used, is set forth in the Examples. Persons of skill in the art will recognize that other sets of primers could readily be designed from the sequence of MTb which would likewise amplify the EtaA gene.

In a particularly preferred embodiment, the EtaA gene can be amplified using the primers 5'-GGGGTACCGACAT-TACGTTGATAGCGTGGA-3' (SEQ ID NO:3) and 5'-ATAAGAATGCGGCCGCAAC-CGTCGCTAAAGCTAAACC-3' (SEQ ID NO:4) (EtaA). Many other primer sets can be selected using standard programs widely available in the art. For example, the program "Primer3" is available on-line by entering "www-" followed by "genome.wi.mit.edu/cgi-bin/primer/primer3_www.cgi." This program was used to select the primer pairs noted above, using the default conditions. The program was also used to select the following sequencing primers, which can be used to amplify sections of the EtaA gene for sequencing:

| | |
|---|---|
| 5' ATCATCCATCCGCAGCAC 3'; | (SEQ ID NO:5) |
| 5' AAGCTGCAGGTTCAACC 3'; | (SEQ ID NO:6) |
| 5' GCATCGTGACGTGCTTG 3'; | (SEQ ID NO:7) |
| 5' AAGCTGCAGGTTCAACC 3'; | (SEQ ID NO:8) |
| 5' TGAACTCAGGTCGCGAAC 3'; | (SEQ ID NO:9) |
| 5' AACATCGTCGTGATCGG 3'; | (SEQ ID NO:10) |
| 5' ATTTGTTCCGTTATCCC 3'; | (SEQ ID NO:11) |
| 5' AACCTAGCGTGTACATG 3'; | (SEQ ID NO:12) |
| 5' TCTATTTCCCATCCAAG 3; and | (SEQ ID NO:13) |
| 5' GCCATGTCGGCTTGATTG 3'. | (SEQ ID NO:14) |

Labeling of Nucleic Acid Probes

Where the EtaA DNA or a subsequence thereof or an mRNA of such DNA is to be used as a nucleic acid probe, it is often desirable to label the sequences with detectable labels. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In another preferred embodiment, transcription amplification using a labeled nucleotide (e.g. fluorescein-labeled UTP and/or CTP) incorporates a label into the transcribed nucleic acids.

Alternatively, a label may be added directly to an original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled DNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Kits

The invention further provides kits for determining the ability of a *M. tuberculosis* bacterium to metabolize a thioamide, thereby permitting a determination of whether the bacterium is susceptible or resistant to thioamide- or thiocarbonyl-based agents. The kits can take any of a variety of forms, such as:

a kit for performing TLC to detect the presence of (2-ethyl-pyridin-4-yl)methanol will usually provide a sample of (2-ethyl-pyridin-4-yl)methanol which can be run in parallel with the experimental sample to provide a positive control;

a kit may provide radiolabeled ETA so that the presence or absence of a product of EtaA metabolism can be detected. For example, the kit may provide $^{14}C$-labeled ETA so that the presence or absence of labeled (2-ethyl-pyridin-4-yl)methanol can be detected;

a kit may provide primers for amplifying an EtaA gene or a portion thereof containing a mutation that affects the ability of the bacterium to oxidize a thioamide, such as 5'-GGGGTACCGACATTACGTTGATAGCGTGGA-3' (SEQ ID NO:3) and 5'-ATAAGAATGCGGCCG-CAACCGTCGCTAAAGCTAAACC-3' (SEQ ID NO:4), or any of the other primer pairs set forth above. It should be noted that, due to the low synonymous rate of mutation of *M. tuberculosis*, it is believed that all naturally-occurring mutations in the EtaA gene will reduce the ability of the organism to oxidize a thioamide. The kit may also include isolated EtaA genes containing one or more mutations from the wild-type sequence (SEQ ID NO:1), or nucleic acid sequences derived from such an EtaA gene, for use as a positive control during PCR or other amplification procedures;
- a kit may provide one or more antibodies which permit the use of ELISAs or other immunoassays known in the art. Typically, the antibodies will be raised against (2-ethyl-pyridin-4-yl)methanol, to permit detection of whether this metabolic product is produced by a particular culture, or antibodies against the gene product of the wild-type EtaA gene, or against a gene product expressed from a missense, nonsense, or frameshift mutation of the EtaA gene.

EXAMPLES

Example 1

Synthesis of 2-ethyl-[$^{14}C$]thioisonicotinamide (1-[$^{14}C$]ETA)

2-ethylpyridine was converted to its N-oxide salt in almost quantitative yield using 35% hydrogen peroxide in acetic acid and the corresponding N-oxide was subjected to a nitrating mixture of sulfuric and nitric acids to form 2-ethyl-4-nitropyridine N-oxide in 60% yield (Kucherova, et al., Zhurnal Obshchei Khimii 29:915-9 (1959). Reduction using iron filings, hydrochloric, and acetic acid (Gutekunst and Gray, J. Am. Chem Soc., 44:1741 (1922)) allowed us to isolate 2-ethyl-4-aminopyridine, which was converted to 2-ethyl-4-bromopyridine through the perbromide using 50% aqueous hydrobromic acid and sodium nitrite (Kucherova et al., supra). The resulting bromide was heated with copper cyanide in N-methylpyrrolidin-2-one to afford 2-ethyl-4-[$^{14}C$]cyanopyridine (Lawrie et al., J Labelled Compounds Radiopharmaceutic 36:891-8 (1995)). [$^{14}C$]-copper cyanide was obtained from [$^{14}C$]-sodium cyanide (Amersham Pharmacia Biotech, Inc., Piscataway, N.J. 08855) using copper (II) sulfate pentahydrate and sodium sulfite (Sunay et al., J Labelled Compounds Radiopharmaceutic 36:529-36 (1995); Meinert et al., J Labelled Compounds Radiopharmaceutic 14:893-6 (1978)). The nitrite was converted to 1-[$^{14}C$]-ETA by hydrogen sulfide treatment and the resulting thioamide was purified to 98% final radiochemical purity using normal phase HPLC with a preparative ADSORBOSPHERE silica column (5μ, 300×22 mm, Alltech Associates, Deerfield, Ill.) and an isochratic eluent of 90% chloroform, 10% methanol. Unlabeled ETA synthesized using the same procedure co-chromatographed with commercially available ETA (Sigma-Aldrich Chemical Company, Milwaukee, Wis.) and showed correct analytical data.

Example 2

Materials and Methods for Determining in vivo Metabolism of 1-[$^{14}C$]ETA The indicated mycobacterial species were grown in culture to an OD650 of 1.0-1.5 and then concentrated 10-fold in middlebrook 7H9 broth media (DIFCO laboratories, Detroit, Mich.). The culture suspensions were treated with 0.01 μg ml$^{-}$1 of [$^{14}C$]-ETA (55 mCi/mmol) and sequential culture aliquots were removed at the indicated times, filtered and flash frozen. Samples of 2 μl were analyzed by TLC on Silica gel 60 plates (EM Science, Gibbstown, N.J. 08027) developed with 95:5 ethyl acetate:ethanol. Prior to spotting radioactive samples on TLC plates a small amount of unlabeled ETA was spotted to circumvent silica-catalyzed air oxidation of the low concentration radioactive ETA samples.

Metabolites were identified by comparison with well characterized synthetic standards prepared as follows: the sulfoxide was prepared by hydrogen peroxide oxidation of ETA as previously described (Walter and Curtis, Chem Ber 93:1511 (1960)). The acid was made by reflux hydrolysis of the thioamide with 30% NaOH (Aq); $^1H$-NMR ($CDCl_3$:$CD_4OD$;1:1); δ 1.26 t, 2.83 q, 7.63 d, 7.71 s, 8.52 d; ES-MS (MH+) 152.1 m/e. The amide (4) was made by treating the corresponding acid chloride with ammonium hydroxide; $^1H$-NMR ($CDCl_3$); δ 1.34 t, 2.91 q, 7.45 d, 7.55 s, 8.65 d; ES-MS ($MH^+$) 151.2 m/e. (2-ethyl-pyridin-4-yl)-methanol (5) was made by RedAl reduction of the acid in THF; $^1H$-NMR ($CDCl^3$); δ 1.28 t, 2.84 q, 7.11 d, 7.19 s, 8.48 d; $^{13}$C-NMR (CDCl$_3$); 14.12, 30.54, 63.92, 118.73, 119.64, 149.25, 150.60, 163.89; ES-MS (MH$^+$) 138.0 m/e.

Cells from sequential culture aliquots from the metabolic conversion assays (volumes given in figure legends) were collected by filtration onto 0.22 micron GS filter disks (Millipore, Bedford, Mass.) under vacuum on a Hoeffer apparatus and were washed twice with 0.1 mM sodium phosphate, pH 7.5, 100 mM NaCl (500 µl). The cell associated radioactivity was measured in 4 ml of EcoscintA scintillation solution (National Diagnostics, Atlanta, Ga.). HPLC separation of the [$^{14}$C]-ETA metabolite mixture was achieved using a reverse-phase LUNA column (5µ, C18(2), 250×4.6 mm, Phenomenex, Torrence, Calif.) with a gradient of: (0-5 min) 0% acetonitrile, 100% water; then (5-65 min) to 70% acetonitrile; then (65-80 min) to 100% acetonitrile (all solvents contained 0.1% trifluoroacetic acid). The retention time of the unknown radiolabeled major metabolite (5) utilizing continuous radio-detection (β-RAM, INUS Systems, Florida), was used to guide cold large scale ETA feeding experiments with up to 1 liter of log phase MTb H37Rv, to which we fed 10 μg ml$^-$ 1 ETA (Sigma-Aldrich, Milwaukee, Wis.). We HPLC isolated very small quantities of unlabeled metabolite with a similar retention time to (5), utilizing $UV_{254}$ detection. The metabolite (5) gave a mass of 137 (137.9 MH+)(Mass spectrometer model API300TQMS, Perkin Elmer/Sciex, Toronto, Canada). For *Mycobacterium smegmatis* ("MSm" or "MSMEG"), macromolecule associated radioactivity was determined by resuspending cells from micro-centrifuged 900 min aliquots (400 μl) in PBS. The cells were ruptured by bead-beating (MiniBeadBeater, BioSpec Products, Bartlesville, Okla., 3×45 sec, 0.1 mm glass beads) and extensively dialyzing the lysates with centricon 10 concentrators (Amicon Inc, Beverly, Mass.) before analysis in 4 ml of EcoscintA scintillation solution.

Example 3

Cloning of EtaA and EtaR

Genomic DNA from MTb H37Rv was partially digested with Sau3AI (New England BioLabs, Beverly, Mass.) to give fragments of various sizes. Fragments ranging from 1 Kb to 10 Kb were ligated to pMV206Hyg (Mdluli et al., J Infect Dis 174:1085-90 (1996)) that had been previously linearized with BamHI (New England BioLabs). The ligation mixtures were electroporated into *Escherichia coli* DH5α (Life Technologies, Grand Island, N.Y.) for amplification of the DNA library which was subsequently purified and electroporated into MTb H37Rv. The resulting transformants were plated on 7H11 (DIFCO) agar plates that contained Hygromycin (Life Technologies, 200 μg ml$^{-1}$) and the indicated concentrations of ETA. Five colonies were isolated that had MICs for ETA from 2.5 to 5.0 μg/ml (the MIC for wild type MTb is 1.0 μg/ml) (Rist, Adv Tuberc Rec 10:69-126 (1960)).

EtaA and EtaR were PCR-amplified from H37Rv chromosomal DNA using the following primers 5'-GGGGTACCGACATTACGTTGATAGCGTGGA-3' (SEQ ID NO:3) and 5'-ATAAGAATGCGGCCGCAACCGTGCTAAAGCTAAACC-3' (SEQ ID NO:4) (Rv3854c, EtaA); 5'-GGGGTACCGCACACTATCGACAC GTAGTAAGC-3' (SEQ ID NO:15) and 5'-ATAAGAATGCGGCCGCGCGGTTCTC GCCGTAAATGCT-3' (SEQ ID NO:16) (EtaR) and inserted directionally into KpnI and NotI digested pMH29 (Mdluli et al., supra).

Example 4

Sequence Analysis of ETA-Resistant Clinical Isolates

Using the primers described in the previous Example, EtaA was PCR amplified from genomic DNA containing, drug resistant isolate lysates (1 ml, bead beaten for 3×45 sec and aqueous diluted 10-fold). EtaA was sequenced in entirety by primer walking for all isolates (SEQWRIGHT Inc, Houston, Tex.) and observed mutations were confirmed on both strands. For the three isolates without mutations in EtaA, EtaR and the intergenic region were also sequenced in entirety without observing any mutations.

Example 5

Synthesis and in vivo Metabolism of [14C]-ethionamide

We synthesized [$^{14}$C]-ETA from 2-ethylpyridine and [$^{14}$C]-sodium cyanide (see Example 1, supra) to study the metabolism of ETA by whole cells of MTb. In the presence of live cells of MTb, ETA is converted through the S-oxide (2) to a single major metabolite (5) as seen by TLC analysis of sequential time points (FIG. 1A). Metabolites corresponding to the S-oxide (2), nitrile (3), and the amide (4) were identified by cochromatography (TLC and HPLC) with standards synthesized by known methods and characterized by 1H-NMR, 13C-NMR and mass spectrometry. These metabolites were produced in small amounts by the cellular oxidation of ETA but they were the dominant products of air oxidation of ETA (compare lanes h and i in FIG. 1A).

In contrast, metabolite 5 was only produced by live cells of MTb and was not seen upon air oxidation of ETA. The thioamide S-oxide 2 was transiently produced in whole cells and appeared temporally to be a precursor of metabolite 5 (FIG. 1B). Cold ETA feeding experiments allowed the isolation of unlabeled metabolite 5 which displayed a molecular mass of 137 by LC-MS (FIG. 1C). We assigned this metabolite as (2-ethyl-pyridin-4-yl)-methanol (5) and confirmed this by co-chromatography (TLC and HPLC) with an authentic synthetic alcohol standard. The upper HPLC trace in FIG. 1C shows the continuous radio-detector output from a sample corresponding to [1-$^{14}$C]ETA that has been air oxidized in media (lane i in FIG. 1A). The lower trace shows a sample from MTb metabolism of [1-$^{14}$C]ETA after 1.5 hr of exposure (lane d in A). The $UV_{254}$ trace of synthetic (2-ethyl-pyridin-4-yl)methanol is superimposed in gray.

The production of metabolite (5) from ETA by tuberculosis is surprising as 4-pyridylmethanol is a major metabolite of INH by whole cells of MTb (Youatt, J. *Aust J Chem* 14:308 (1961); Youatt, J. *Aust J Exp Biol Med Sci* 38:245 (1960); Youatt, J. *Aust J Biol Med Sci* 40:191(1962)). Like spontaneous oxidation of INH, spontaneous oxidation of ETA fails to produce any trace of the major in vivo metabolite, (2-ethyl-pyridin-4-yl)methanol. INH has been shown to be activated by KatG in vitro to a variety of products including isonicotinic acid, isonicotinamide and isonicotinaldehyde (which in vivo is rapidly reduced to 4-pyridylmethanol) (Johnsson, K. et al., *J Am Chem Soc* 116:7425 (1994)). INH metabolism to 4-pyridylmethanol only occurs in drug-susceptible organisms while drug-resistant organisms no longer produce this metabolite (Youatt, J., *Am Rev Respir Dis* 99:729 (1969)). Similarly, we postulate that ETA is activated via the corresponding S-oxide to a sulfinate that can form an analogous aldehyde equivalent (an imine) through a radical intermediate (Paez, O. A. et al., *J Org Chem* 53:2166 (1988)).

Example 6

Identification of a Monooxygenase that Activates ETA

To elucidate the enzymatic basis for activation of ETA to metabolite 5 by MTb we selected for ETA resistance in MTb by transformation of a 1-10 kb insert-containing library of MTb chromosomal DNA in pMV206Hyg (George et al., J. Biol. Chem. 270:27292-8 (1995)). Five colonies were isolated that had MICs for ETA from 2.5 to 5.0 μg/ml (the MIC for wild type MTb is 1.0 μg/ml). Upon restriction analysis the five independent plasmids were shown to contain the same genomic region on different overlapping Sau3AI fragments. This cloning was also done with genomic DNA from a strain reported to be ETA-resistant but the same genomic locus was obtained with no alterations compared to H37Rv, suggesting that the resistance was not associated with alterations to this region but simply with its overexpression. The common region to all the resistance-conferring clones encompassed only one gene (Rv3855, EtaR) that showed broad homology to many TetR family transcriptional regulators. A 76 nt intergenic region separates this putative regulator from a divergently transcribed monooxygenase (Rv3854c, EtaA). One of the isolated library plasmids containing only the etaR gene was electroporated into MTb and MSm and the resulting MTb transformants grew as a lawn at 2.5 and 5 μg/ml ETA indicating that EtaR was solely responsible for ETA resistance. The MSm transformants were able to grow at greater than 200 μg/ml ETA, compared to growth of vector control containing MSm at 50 μg/ml.

Two other monooxygenase/regulator pairs with similar genomic organization appeared to have high homology in both the regulator and monooxygenase components to the MTb locus, one from *Dienococcus radiodurans* (White et al., Science 286:1571-7 (1999)) and the other from *Streptomyces coelicolor* (Redenbach et al., Mol Microbiol 21:77-96 (1996). This conservation suggested that the effect of regulator expression was to modulate production of the adjacent monooxygenase. To see if EtaR-mediated repression of EtaA was the cause of ETA resistance, we transformed MTb and MSm with pMH29 plasmid constructs containing etaR and EtaA separately under the control of a strong constituitive promoter (Mdluli et al., supra). Although we could observe resistance with EtaR constructs in MTb, we were not successful in overexpressing EtaA in MTb, suggesting expression of this enzyme is tightly controlled in this organism. MSm overexpressing the putative repressor was found to be ETA resistant with a measured MIC greater than 62.5 μg/ml on solid media (FIG. 2A). Although the recombinant MSm were equally susceptible to killing with INH, the bacteria overexpressing EtaA were found to be hypersensitive to ETA with noticeable growth inhibition at 2.5 μg/ml, a level comparable to the normal MIC for MTb (FIG. 2A). Qualitatively comparable results were obtained when these organisms were treated with ETA S-oxide (although the absolute MIC for the sulfoxide is lower, EtaR conferred resistance and EtaA conferred hypersensitivity). These results suggest that EtaA is directly responsible for thioamide S-oxide oxidative activation and that EtaR modulates expression of this enzyme.

Example 7

Effect of the EtaR Gene

To link expression of the EtaA activator more directly with ETA metabolism we examined [$^{14}$C]-ETA conversion by whole cells of the MSm transformants described above over a time-course study as shown in FIG. 3. The EtaA overproducing MSm was found to convert ETA to metabolite 5 much more quickly than vector control (FIG. 3A). Although the EtaR overproducing strain did appear to effect this conversion less efficiently than the control, the result was not dramatic since MSm normally only weakly activates ETA consistent with this organism's higher overall MIC for ETA (FIG. 1B). These studies directly correlate ETA activation and metabolism with toxicity as measured by MIC. To understand the effect of drug activation we also examined covalent incorporation of [$^{14}$C]-ETA into cellular macromolecules by lysing treated cells and then extensively dialyzing away small molecules. Drug activation was found to correlate directly with incorporation of labeled drug into macromolecules (FIG. 2D).

Example 8

Correlation of ETA-Resistance with Resistance to other Thioamide Drugs

ETA is only one example of a thiocarbonyl-containing antituberculosis medication approved for clinical use. Among the second-line tuberculosis therapeutics there are two other such molecules, thiacetazone (11) and thiocarlide (isoxyl) (12) (FIG. 4A) that might be similarly activated by EtaA-catalyzed S-oxidation. To elucidate the clinical relevance of EtaA-mediated resistance to thiocarbonyl-containing drugs as a class we characterized a set of 14 multidrug resistant isolates from patients in Cape Town, South Africa. These isolates were selected on the basis of thiacetazone resistance and then characterized with respect to ETA resistance. Eleven of fourteen of these isolates were found to be ETA cross-resistant. Despite the fact that none of the patients had been treated with thiocarlide, thirteen out of fourteen of the isolates showed thiocarlide cross-resistance.

To examine at the molecular level the relevance of EtaA-mediated thiocarbonyl activation for this class of compounds, we PCR-amplified and sequenced the EtaA gene from all 14 multidrug-resistant patient isolates. In addition, we examined an in vitro generated ETA mono-resistant strain (ATCC 35830). Eleven of 14 clinical isolates had amino acid altering mutations in EtaA, as indicated in FIG. 4B.

EtaA was PCR amplified from chromosomal DNA-containing lysates of 1 ml cultures of patient isolates using the primers set forth in Example 1, above. EtaA was sequenced in its entirety by primer walking for all isolates and observed mutations were confirmed on both strands. For the three isolates without mutation in EtaA, EtaR and the intergenic region were also sequenced in their entirety without observing any mutations. Eleven of fourteen clinical isolates had amino acid-altering mutations in EtaA, as indicated in FIG. 3A. The nucleotide change at base 1025 was found in two isolates, that at base 1141 in three isolates. Along with the single nucleotide changes, a 1 nt nucleotide deletion (at base 65) and addition (at base 811) were found. In the ATCC ETA mono-resistant strain, a nucleotide change at position 557 of EtaA was found. The patient isolates in which mutations could not be found (either in EtaA, EtaR or their promoter regions) were subsequently tested and found to be fully sensitive to ETA. Thus there is a 100% correspondence between mutation in EtaA and ETA cross-resistance among these thiacetazone-resistant strains.

Example 9

Mechanism of ETA Activation

INH (6) has been shown to be activated by KatG in vitro to a variety of products including isonicotinic acid, isonicotinamide and isonicotinaldehyde (9) (which in vivo is rapidly reduced to 4-pyridylmethanol (10)) (Johnsson, K. & Schultz, P. G., J Am Chem Soc 116:7425-68 (1994)). The results support the notion that in vivo INH is metabolized by oxidation to an acyl diimide (7), then to a diazonium ion (8) or an isonicotinyl radical which may abstract a hydrogen atom from a suitable donor to form isonicotinaldehyde. Similarly, we postulate that ETA is activated via the corresponding S-oxide (2) to a sulfinate that can form an analogous aldehyde equivalent (an imine) through a radical intermediate. Hydrolysis of this imine could be followed by reduction of the resulting aldehyde to the observed metabolite (5).

The mechanistic linkage of the activated form of ETA and INH explains, in part, the observation that they share a final common target. The striking observation that both drugs give rise to essentially the same final metabolite upon productive activation of the drug, further substantiates this common mechanism. Despite this commonality, an acyl hydrazide and a thioamide must undergo very different activation processes by discrete enzymes before they converge upon an analogous reactive intermediate. The association of KatG with INH activation has been firmly established by a combination of loss of activity studies, laboratory-selected drug-resistant mutants, overexpression, and clinically relevant mutations. The results here establish that EtaA is the analogous enzyme for the activation of ETA and provide similar evidence based upon genetic manipulation of the enzyme levels and mutations observed in patient isolates.

Example 10

Relationship of EtaA to other Bacterial Enzymes

EtaA has two closely related homologs (Rv3083, Rv0565c) encoded within the MTb genome that share almost 50% identity to this monooxygenase (Cole, et al., Nature 393:537-44 (1998)). It is also a member of a family of 14 more loosely related proteins, the majority of which are probable monooxygenases. In addition, MTb has twenty additional homologs of Cytochrome P-450 containing oxygenases, the largest number ever identified within a single bacterial genome (Nelson, D. R., Arch Biochem Biophys 369:1-10 (1999)). The reason for this amazing radiation of oxidative enzymes is not clear but they may improve bacterial survival in the face of various xenobiotic substances. In this vein, the ETA susceptibility of this organism may arise from accidental activation by an enzyme intended to help detoxification.

Thiacetazone (11) has been widely used as a front-line therapeutic in Africa and throughout the developing world because it is extremely inexpensive. Although thiocarlide (12) has not been widely used there is renewed interest in this drug and new analogs. There is an impressive clinical history of cross-resistance among this set of three second-line therapies. This cross-resistance suggested a common mechanism of activation of thiocarbonyl containing molecules that might allow the simultaneous acquisition of drug resistance to this class of therapeutic. When we examined patient isolates from Cape Town for cross-resistance to other thioamides or thioureas, we noted that the vast majority of ETA/thiacetazone resistant isolates were already resistant to thiocarlide, despite the fact that these patients were never treated with this drug.

The extensive cross-resistance among these compounds predicts multiple overlapping mechanisms of resistance among clinically used antituberculars: target associated between INH and ETA, and activation-associated between ETA, thiacetazone, and thiocarlide. Such considerations complicate appropriate drug therapy for the treatment of multidrug-resistant tuberculosis and these results provide an important tool to help understand and quickly characterize the resistance mechanisms operating in a single patient, which may prove vital to a positive outcome.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining the ability of a *Mycobacterium tuberculosis* bacterium to oxidize a thioamide or a thiocarbonyl, said method comprising detecting a mutation in an EtaA gene (SEQ ID NO:1) in said bacterium by detecting a product of said gene altered from the sequence of SEQ ID NO:2, wherein detection of the gene product alteration is indicative of decreased ability to oxidize a thioamide or a thiocarbonyl.

2. The method of claim 1, wherein the gene product alteration results from a frameshift mutation selected from the group consisting of: a deletion at position 65, an addition at position 557, and an addition at position 811.

3. The method of claim 1, wherein the gene product alteration results from a single nucleotide polymorphism.

4. The method of claim 3, wherein the single nucleotide polymorphism causes an amino acid substitution selected from the group consisting of: G43C, P51L, D58A, Y84D, T186K, T342K, and A381P.

5. A method of claim 1, wherein said mutation is detected by specifically binding an antibody to a mutated product of the EtaA gene, wherein the specific binding of the antibody to the mutated gene product is indicative of a mutation which inhibits the ability of the bacterium to oxidize a thioamide.

6. A method of claim 1, wherein said gene product is in, or is isolated from, sputum.

7. A method of claim 5, wherein detection of said specific binding of said antibody and said mutated gene product is by ELISA.

8. A method of claim 1, wherein said thioamide or thiocarbonyl is selected from the group consisting of etbionamide, thiacetazone, and thiocarlide.

9. A method of claim 1, wherein said mutation is detected by
   (a) culturing said bacterium in the presence of ethionamide; and
   (b) testing for the presence or absence of (2-ethyl-pyridin-4-yl)methanol,
wherein the absence of (2-ethyl-pyridin-4-yl)methanol indicates that the bacterium has a mutation which is indicative of decreased ability to oxidize a thioamide.

10. A method of claim 9, wherein the presence or absence of (2-ethyl-pyridin-4-yl)methanol is tested by subjecting a medium in which the bacterium is cultured, or the bacterium, to analysis by thin-layer chromatography, high pressure liquid chromatography, or mass spectrometry.

11. A method of claim 9, wherein the ethionamide of step (a) is radioactively labeled.

12. A method of claim 9, wherein the (2-ethyl-pyridin-4-yl)methanol is radioactively labeled.

13. A method of claim 1, wherein said mutation is detected by specifically binding an antibody to a mutated product of the EtaA gene selected from the group of mutations consisting of
   (a) a frameshift mutation consisting of a deletion at position 65, an addition at position 557, and an addition at position 811, and
   (b) a single nucleotide polymorphism which causes an amino acid substitution selected from the group consisting of: G43C, P51L, D58A, Y84D, T186K, T342K, and A381P, wherein the specific binding of the antibody to the mutated gene product is indicative of a mutation which inhibits the ability of the bacterium to oxidize a thioamide.

* * * * *